(12) United States Patent
Maliga et al.

(10) Patent No.: US 7,217,860 B1
(45) Date of Patent: May 15, 2007

(54) SITE-SPECIFIC RECOMBINATION SYSTEM TO MANIPULATE THE PLASTID GENOME OF HIGHER PLANTS

(75) Inventors: Pal Maliga, East Brunswick, NJ (US); Sylvie Corneille, Highland Park, NJ (US); Kerry Lutz, Lawrenceville, NJ (US)

(73) Assignee: Rutgers, The State University of New Jersey, New Brunswick, NJ (US)

( * ) Notice: Subject to any disclaimer, the term of this patent is extended or adjusted under 35 U.S.C. 154(b) by 942 days.

(21) Appl. No.: 10/088,634

(22) PCT Filed: Sep. 21, 2000

(86) PCT No.: PCT/US00/25930

§ 371 (c)(1),
(2), (4) Date: Oct. 16, 2002

(87) PCT Pub. No.: WO01/21768

PCT Pub. Date: Mar. 29, 2001

Related U.S. Application Data

(60) Provisional application No. 60/155,007, filed on Sep. 21, 1999, provisional application No. 60/211,139, filed on Jun. 13, 2000.

(51) Int. Cl.
*C12N 15/82* (2006.01)
*C12N 15/00* (2006.01)
*A01H 5/00* (2006.01)
*C12N 5/10* (2006.01)

(52) U.S. Cl. ............... 800/288; 435/320.1; 435/468

(58) Field of Classification Search ............ 435/320.1, 435/419, 468; 800/278, 295
See application file for complete search history.

(56) References Cited

U.S. PATENT DOCUMENTS

| | | | |
|---|---|---|---|
| 5,614,395 A | 3/1997 | Ryals et al. | |
| 5,877,402 A | 3/1999 | Maliga et al. | |
| 6,297,054 B1 | 10/2001 | Maliga et al. | |
| 6,376,744 B1 | 4/2002 | Maliga et al. | |
| 6,388,168 B1 | 5/2002 | Maliga et al. | |
| 6,472,586 B1 | 10/2002 | Maliga et al. | |

OTHER PUBLICATIONS

Corneille et al., Plant J., 2001, vol. 27, pp. 171-178.*
Kilby et al., Trends in Gen., 1993, vol. 9, pp. 413-421.*
Khan, M.S. "Fluorescent antibiotic resistance marker for tracking plastid transformation in higher plants"; Nature Biotechnology, 17: 910-915 (1999).
Dale, E.C. "Gene transfer with subsequent removal of the selection gene from the host genome", Proc. Natl. Acad. Sci. USA, 88: 10558-10562 (1991).
Srivastava, V. "Single-copy transgenic wheat generated through the resolution of complex integration patterns"; Proc. Natl. Acad. Sci. USA, 96: 11117-11121 (1999).
Le, Y. "Nuclear targeting determinants of the phage P1 Cre DNA recombinase"; Nucleic Acids Research, 27(24): 4703-4709 (1999).
Lyznik, L.A. "Activity of yeast FLP recombinase in maize and rice protoplasts"; Nucleic Acids Research, 21(4): 969-975 (1993).
Lyznik, L.A. "FLP-mediated recombination of FRT sites in the maize genome"; Nucleic Acids Research, 24(19): 3784-3789 (1996).
Zoubenko, O.V. "Efficient targeting of foreign genes into the tobacco plastid genome"; Nucleic Acids Research, 22(19): 3819-3824 (1994).
Love, J. "Stringent control of transgene expression in *Arabidopsis thaliana* using the Top10 promoter system"; The Plant Journal, 21(6): 579-588 (2000).
Serino, G. "A negative selection scheme based on the expression of cytosine deaminase in plastids"; The Plant Journal, 12(3): 697-701 (1997).
Lyznik, L.A. "Heat-inducible expression of FLP gene in maize cells"; The Plant Journal, 8(2): 177-186 (1995).
Soll, J. "Protein translocation into and across the chloroplastic envelope membranes"; Plant Molecular Biology, 38: 191-207 (1998).
Adams, D. "Cre-lox Recombination in *Escherichia coli* Cells Mechanistic Differences from the in Vitro Reaction"; J. Mol. Biol., 226: 661-673 (1992).
Craig, N.L. "The Mechanism of Conservative Site-Specific Recombination"; Annu. Rev. Genet., 22: 77-105 (1988).
Lichtenstein, C. "Prospects for reverse genetics in plants using recombination"; Plant Molecular Biology, 21: v-xii (1993).
Lubben, T.H. "Chloroplast import characteristics of chimeric proteins"; Plant Molecular Biology; 12: 13-18 (1989).
Russell, S.H. "Directed excision of a transgene from the plant genome"; Mol Gen Genet, 234: 45-59 (1992).
Timko, M.P. "Structure and Expression of Nuclear Genes Encoding Polypeptides of the Photosynthetic Apparatus"; Mol Biol of the Photosynthetic Apparatus, 381-396 (1985).
Timmermans, M.C.P. "The pFF plasmids: cassettes utilising CaMV sequences for expression of foreign genes in plants"; Journal of Biotechnology, 14: 333-344 (1990).
Wasmann, C.C. "The Importance of the transit peptide and the transported protein for protein import into chloroplasts"; Mol Gen Genet, 205: 446-453 (1986).

* cited by examiner

*Primary Examiner*—Ashwin Mehta
(74) *Attorney, Agent, or Firm*—Dann Dorfman Herrell and Skillman; Kathleen D. Rigaut

(57) ABSTRACT

A site-specific recombination system and methods of use thereof are disclosed for manipulating the plastid genome of higher plants.

21 Claims, 20 Drawing Sheets

SITE-SPECIFIC RECOMBINATION SYSTEM TO MANIPULATE THE PLASTID GENOME OF HIGHER PLANTS

This application is a §371 filing of PCT/US00/25930 filed Sep. 21, 2000 which in turn claims priority to U.S. provisional application 60/155,007 and 60/211,139 filed Sep. 21, 1999 and Jun. 13, 2000, respectively, each of which is incorporated by reference herein.

FIELD OF THE INVENTION

This invention relates to the fields of transgenic plants and molecular biology. More specifically, DNA constructs and methods of use thereof are provided which facilitate the excision of target DNA sequences from transplastomic plants.

BACKGROUND OF THE INVENTION

Several publications are referenced in this application by author name and year of publication in parentheses in order to more fully describe the state of the art to which this invention pertains. Full citations for these reference can be found at the end of the specification. The disclosure of each of these publications is incorporated by reference herein.

The plastid genetic system of higher plants is highly polyploid. For example, in a tobacco leaf there are as many as 100 chloroplasts, each carrying ~100 identical genome copies, a total of 10,000 copies in a leaf cell. High-level protein expression, lack of pollen transmission and the feasibility to engineer polycistronic expression units make the plastid genome an attractive alternative to nuclear engineering. Plastid transformation vectors often contain a selective marker, most commonly a spectinomycin resistance (aadA) gene, flanked by plastid DNA sequences targeting insertion of the marker gene by homologous recombination into the plastid gnome. Genes of commercial value but lacking a selectable phenotype are physically linked to the selective marker and the two genes are integrated together as a block of heterologous sequences. Plastid transformation is accomplished by biolistic DNA delivery or polyethylene glycol induced uptake of the transforming DNA followed by selection for the antibiotic resistance marker to ensure preferential propagation of plastids with transformed genome copies. As the result, all the 10,000 wild-type plastid genome copies in a cell are replaced with transgenic copies during a gradual process (Maliga, 1993).

Incorporation of a selectable marker gene is essential to ensure preferential maintenance of the transformed plastid genome copies. However, once transformation is accomplished, maintenance of the marker gene is undesirable. One problem may be the metabolic burden imposed by the expression of the selectable marker gene. For example FLARE-S, the product of the marker gene with good prospects to transform cereal chloroplasts, accumulates up to 18% of the total soluble cellular protein (Khan and Maliga 1999). The second problem is the relatively high potential for horizontal transfer of plastid marker genes to microbes (Tepfer 1989; Dröge et al. 1998; Sylvanen 1999), as commonly used plastid maker gene constructs are efficiently expressed in *E. coli* (Carrer et al. 1993; Svab and Maliga 1993). Therefore, having plastid marker genes in commercial products is undesirable.

SUMMARY OF THE INVENTION

In accordance with the present invention, methods and systems are provided which facilitate the manipulation of the plastid genomes of higher plants. The methods and systems of the invention may be employed to remove heterologous sequences from the plastid genome, such as selectable marker genes following successful isolation of transformed progeny. Alternatively, they may be designed to remove endogenous genes involved in plant cell metabolism, growth, development and fertility.

In one embodiment of the invention, a site specific recombination method for removal of predetermined nucleic acid sequences from the plastid genome is provided. The method comprises providing a first nucleic acid construct, the construct comprising a promoter being operably linked to a nucleic acid encoding an optional plastid targeting transit sequence which is in turn operably linked to a nucleic acid encoding a protein having excision activity, the construct further comprising a first selectable marker encoding nucleic acid having plant specific 5' and 3' regulatory nucleic acid sequences. The method also entails the use of a second DNA construct, the second construct comprising an second selectable marker encoding nucleic acid and excision sites. The second construct optionally contains a gene of interest and further comprises flanking plastid targeting nucleic acid sequences which facilitate homologous recombination into said plastid genome. The second DNA construct is introduced into plant cell and the cells are cultured in the presence of a selection agent, thereby selecting for those plant cells expressing the proteins encoded by said second DNA construct. The first DNA construct is then introduced into cells having the second construct in the presence of a selection agent and those plant cells expressing proteins encoded by said first construct are selected. If present, the excising activity acts on the excision sites, thereby excising said predetermined target sequence. Plants may then be regenerated from plant cells obtained by the foregoing method.

Proteins having excision activity suitable for the practice of the invention include, without limitation, CRE, flippase, resolvase, FLP, SSV1-encoded integrase, and transposase. Sequences corresponding to excision sites suitable for the practice of the invention, include, for example, LOX sequences, and frt sequences.

A variety of selection of agents may be selected. These include without limitation, kanamycin, gentamycin, spectinomycin, streptomycin and hygromycin, phosphinotricin, basta, glyphosate and bromoxynil.

In an alternative embodiment, a site specific recombination method for removal of predetermined nucleic acid sequences from the plastid genome is provided. The method comprising providing a first nucleic acid construct, said construct comprising a regulated promoter being operably linked to a nucleic acid encoding an optional plastid targeting transit sequence which is operably linked to a nucleic acid encoding a protein having excision activity, said construct optionally further comprising a first selectable marker encoding nucleic acid having plant specific 5' and 3' regulatory nucleic acid sequences. A second DNA construct is also provided, said second construct comprising an second selectable marker encoding nucleic acid and excision sites, said second construct further comprising flanking plastid targeting nucleic acid sequences which facilitate homologous recombination into said plastid genome at a predetermined target sequence such that excision sites flank said predetermined target sequence following homologous recombination and introducing said second DNA construct into a plant cell. The plant cell so generated is then cultured in the presence of a selection agent, thereby selecting for those plant cells expressing the proteins encoded by said second DNA construct. A plant is then regenerated from cells containing the second construct and the first DNA construct is introduced into these cells in the presence of a selection agent and those plant cells expressing proteins encoded by said first construct are selected. The excising activity then acts on the excision sites, thereby excising said predetermined target sequence.

Regulatable promoters suitable for this embodiment of the invention include, without limitation, inducible promoters, tissue specific promoters, developmentally regulated promoters and chemically inducible promoters.

Candidate predetermined target sequences, may include for example genes associated with male sterility, clpP, ribosomal proteins, ribosomal operon sequences.

BRIEF DESCRIPTION OF THE DRAWINGS

FIG. 8A: The coda region was amplified with the O1/O2 primers: the size of aadA-codA fragment is 2.0 kb; the coda deletion fragment is 0.7 kb (FIG. 4). FIG. 8B: Testing for cre sequences by PCR amplification with the Cre1/Cre3 oligonucleotides.

DETAILED DESCRIPTION OF THE INVENTION

Figure 1:
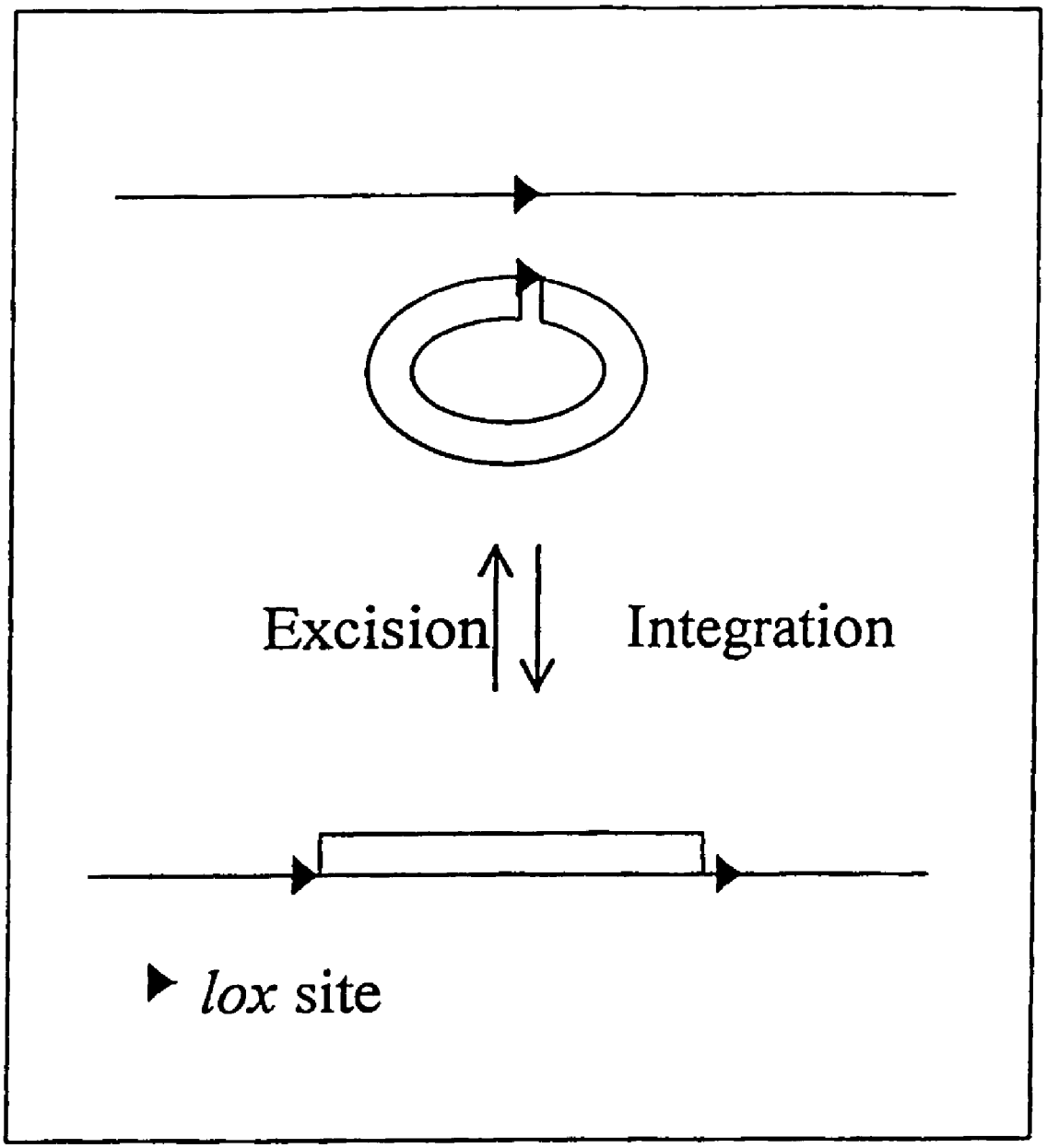
FIG. 1 is a schematic diagram depicting CRE-mediated excision and integration of DNA segments.

The following definitions are provided to aid in understanding the subject matter regarded as the invention.

Heteroplastomic refers to the presence of a mixed population of different plastid genomes within a single plastid or in a population of plastids contained in plant cells or tissues.

Homoplastomic refers to a pure population of plastid genomes, either within a plastid or within a population contained in plant cells and tissues. Homoplastomic plastids, cells or tissues are genetically stable because they contain only one type of plastid genome. Hence, they remain homoplastomic even after the selection pressure has been removed, and selfed progeny are also homoplastomic. For purposes of the present invention, heteroplastomic populations of genomes that are functionally homoplastomic (i.e., contain only minor populations of wild-type DNA or transformed genomes with sequence variations) may be referred to herein as "functionally homoplastomic" or "substantially homoplastomic." These types of cells or tissues can be readily purified to a homoplastomic state by continued selection.

Plastome refers to the genome of a plastid.

Transplastome refers to a transformed plastid genome.

Transformation of plastids refers to the stable integration of transforming DNA into the plastid genome that is transmitted to the seed progeny of plants containing the transformed plastids.

Selectable marker gene refers to a gene that upon expression confers a phenotype by which successfully transformed plastids or cells or tissues carrying the transformed plastid can be identified.

Transforming DNA refers to homologous DNA, or heterologous DNA flanked by homologous DNA, which when introduced into plastids becomes part of the plastid genome by homologous recombination.

Operably linked refers to two different regions or two separate genes spliced together in a construct such that both regions will function to promote gene expression and/or protein translation.

"Nucleic acid" or a "nucleic acid molecule" as used herein refers to any DNA or RNA molecule, either single or double stranded and, if single stranded, the molecule of its complementary sequence in either linear or circular form. In discussing nucleic acid molecules, a sequence or structure of a particular nucleic acid molecule may be described herein according to the normal convention of providing the sequence in the 5' to 3' direction. With reference to nucleic acids of the invention, the term "isolated nucleic acid" is sometimes used. This term, when applied to DNA, refers to a DNA molecule that is separated from sequences with which it is immediately contiguous in the naturally occurring genome of the organism in which it originated. For example, an "isolated nucleic acid" may comprise a DNA molecule inserted into a vector, such as a plasmid or virus vector, or integrated into the genomic DNA of a prokaryotic or eukaryotic cell or host organism.

When applied to RNA, the term "isolated nucleic acid" refers primarily to an RNA molecule encoded by an isolated DNA molecule as defined above. Alternatively, the term may refer to an RNA molecule that has been sufficiently separated from other nucleic acids with which it would be associated in its natural state (i.e., in cells or tissues). An isolated nucleic acid (either DNA or RNA) may further represent a molecule produced directly by biological or synthetic means and separated from other components present during its production.

The terms "percent similarity", "percent identity" and "percent homology" when referring to a particular sequence are used as set forth in the University of Wisconsin GCG software program.

The term "functional" as used herein implies that the nucleic or amino acid sequence is functional for the recited assay or purpose.

The phrase "consisting essentially of" when referring to a particular nucleotide or amino acid means a sequence having the properties of a given SEQ ID No. For example, when used in reference to an amino acid sequence, the phrase includes the sequence per se and molecular modifications that would not affect the basic and novel characteristics of the sequence.

A "replicon" is any genetic element, for example, a plasmid, cosmid; bacmid, phage or virus, that is capable of replication largely under its own control. A replicon may be either RNA or DNA and may be single or double stranded.

A "vector" is a replicon, such as a plasmid, cosmid, bacmid, phage or virus, to which another genetic sequence or element (either DNA or RNA) may be attached so as to bring about the replication of the attached sequence or element.

An "expression operon" refers to a nucleic acid segment that may possess transcriptional and translational control sequences, such as promoters, enhancers, translational start signals (e.g., ATG or AUG codons), polyadenylation signals, terminators, and the like, and which facilitate the expression of a polypeptide coding sequence in a host cell or organism.

The term "oligonucleotide," as used herein refers to primers and probes of the present invention, and is defined as a nucleic acid molecule comprised of two or more ribo- or deoxyribonucleotides, preferably more than three. The exact size of the oligonucleotide will depend on various factors and on the particular application and use of the oligonucleotide.

The term "probe" as used herein refers to an oligonucleotide, polynucleotide or nucleic acid, either RNA or DNA, whether occurring naturally as in a purified restriction enzyme digest or produced synthetically, which is capable of annealing with or specifically hybridizing to a nucleic acid with sequences complementary to the probe. A probe may be either single-stranded or double-stranded. The exact length of the probe will depend upon many factors, including temperature, source of probe and use of the method. For example, for diagnostic applications, depending on the complexity of the target sequence, the oligonucleotide probe typically contains 15–25 or more nucleotides, although it may contain fewer nucleotides. The probes herein are selected to be "substantially" complementary to different strands of a particular target nucleic acid sequence. This means that the probes must be sufficiently complementary so as to be able to "specifically hybridize" or anneal with their respective target strands under a set of pre-determined conditions. Therefore, the probe sequence need not reflect the exact complementary sequence of the target. For example, a non-complementary nucleotide fragment may be attached to the 5' or 3' end of the probe, with the remainder of the probe sequence being complementary to the target strand. Alternatively, non-complementary bases or longer sequences can be interspersed into the probe, provided that the probe sequence has sufficient complementarity with the sequence of the target nucleic acid to anneal therewith specifically.

The term "primer" as used herein refers to an oligonucleotide, either RNA or DNA, either single-stranded or double-stranded, either derived from a biological system, generated by restriction enzyme digestion, or produced synthetically which, when placed in the proper environment, is able to functionally act as an initiator of template-dependent nucleic acid synthesis. When presented with an appropriate nucleic acid template, suitable nucleoside triphosphate precursors of nucleic acids, a polymerase enzyme, suitable cofactors and conditions such as a suitable temperature and pH, the primer may be extended at its 3' terminus by the addition of nucleotides by the action of a polymerase or similar activity to yield an primer extension product. The primer may vary in length depending on the particular conditions and requirement of the application. For example, in diagnostic applications, the oligonucleotide primer is typically 15–25 or more nucleotides in length. The primer must be of sufficient complementarity to the desired template to prime the synthesis of the desired extension product, that is, to be able anneal with the desired template strand in a manner sufficient to provide the 3' hydroxyl moiety of the primer in appropriate juxtaposition for use in the initiation of synthesis by a polymerase or similar enzyme. It is not required that the primer sequence represent an exact complement of the desired template. For example, a non-complementary nucleotide sequence may be attached to the 5' end of an otherwise complementary primer. Alternatively, non-complementary bases may be interspersed within the oligonucleotide primer sequence, provided that the primer sequence has sufficient complementarity with the sequence of the desired template strand to functionally provide a template-primer complex for the synthesis of the extension product. Amino acid residues described herein are preferred to be in the "L" isomeric form. However, residues in the "D" isomeric form may be substituted for any L-amino acid residue, provided the desired properties of the polypeptide are retained.

All amino-acid residue sequences represented herein conform to the conventional left-to-right amino-terminus to carboxy-terminus orientation.

The term "tag," "tag sequence" or "protein tag" refers to a chemical moiety, either a nucleotide, oligonucleotide, polynucleotide or an amino acid, peptide or protein or other chemical, that when added to another sequence, provides additional utility or confers useful properties, particularly in the detection or isolation, to that sequence. Thus, for example, a homopolymer nucleic acid sequence or a nucleic acid sequence complementary to a capture oligonucleotide may be added to a primer or probe sequence to facilitate the subsequent isolation of an extension product or hybridized product. In the case of protein tags, histidine residues (e.g., 4 to 8 consecutive histidine residues) may be added to either the amino- or carboxy-terminus of a protein to facilitate protein isolation by chelating metal chromatography. Alternatively, amino acid sequences, peptides, proteins or fusion partners representing epitopes or binding determinants reactive with specific antibody molecules or other molecules (e.g., flag epitope, c-myc epitope, transmembrane epitope of the influenza A virus hemaglutinin protein, protein A, cellulose binding domain, calmodulin binding protein, maltose binding protein, chitin binding domain, glutathione S-transferase, and the like) may be added to proteins to facilitate protein isolation by procedures such as affinity or immunoaffinity chromatography. Chemical tag moieties include such molecules as biotin, which may be added to either nucleic acids or proteins and facilitates isolation or detection by interaction with avidin reagents, and the like. Numerous other tag moieties are known to, and can be envisioned by, the trained artisan, and are contemplated to be within the scope of this definition.

As used herein, the terms "reporter," "reporter system", "reporter gene," or "reporter gene product" shall mean an operative genetic system in which a nucleic acid comprises a gene that encodes a product that when expressed produces a reporter signal that is a readily measurable, e.g., by biological assay, immunoassay, radioimmunoassay, or by calorimetric, fluorogenic, chemiluminescent or other methods. The nucleic acid may be either RNA or DNA, linear or circular, single or double stranded, antisense or sense polarity, and is operatively linked to the necessary control elements for the expression of the reporter gene product. The required control elements will vary according to the nature of the reporter system and whether the reporter gene is in the form of DNA or RNA, but may include, but not be limited to, such elements as promoters, enhancers, translational control sequences, poly A addition signals, transcriptional termination signals and the like.

The terms "transform", "transfect", "transduce", shall refer to any method or means by which a nucleic acid is introduced into a cell or host organism and may be used interchangeably to convey the same meaning. Such methods include, but are not limited to, transfection, electroporation, microinjection, PEG-fusion, biolistic bombardment and the like.

A "clone" or "clonal cell population" is a population of cells derived from a single cell or common ancestor by mitosis.

A "cell line" is a clone of a primary cell or cell population that is capable of stable growth in vitro for many generations.

Cre-Mediated Site Specific Recombination

The plastid genome of higher plants is present in 100–10,000 copies per cell. Incorporation of a selectable marker gene is essential to ensure preferential maintenance of the transformed plastid genome copies carrying useful genes with no selectable phenotype. However, once transformation is accomplished, maintenance of the marker gene is undesirable. In accordance with the present invention, a bacteriophage PlCRE-loxP site-specific recombination system is provided which is suitable for efficient elimination of marker genes from the plastid genome. The system exemplified herein has two components: a plastid tester strain carrying a cytosine deaminase (coda) transgene flanked by lox sites conferring sensitivity to 5-fluorocytosine and a nuclear CRE line carrying a nuclear-encoded, plastid-targeted CRE. Both the plastid tester (no CRE activity) and the nuclear CRE line (no lox sequence) were genetically stable. However, coda was eliminated at a very fast rate when the plastid-targeted CRE was introduced into the plastid tester strain by transformation or crossing. The gene for the nuclear-encoded CRE was subsequently separated from the transformed plastids by segregation in the seed progeny. Excision of coda by CRE was often accompanied by deletion of a plastid genome segment flanked by short directly repeated sequences. Removal of the antibiotic resistance marker from the transplastomic plants eliminates the metabolic burden imposed by the expression of the selectable marker gene and should also improve public acceptance of the transgenic crops. Additional applications of the CRE-lox site-specific recombination system are activation of plastid gene expression by deletion or inversion of plastid genome sequences and induction of controlled cell death by deleting vital genes in the male reproductive tissue.

Although the use the CRE recombinase is exemplified herein, other prokaryotic and eukaryotic site-specific recombinases would be equally suitable for the elimination of the marker genes.

Recently, several prokaryotic and lower eukaryotic site-specific recombination systems have been shown to operate successfully in higher eukaryotes. In plant and animal cells functional site-specific recombination systems from bacteriophages P1 (Cre-lox) Mu (Gin-gix), and from the inversion plasmids of *Saccharomyces cerevisiae* (FLP-frt) (Morris et al. 1991; O'Gorman et al. 1991; Lichtenstein and Barrena 1993; Lyznik et al. 1993; Lyznik et al. 1995; Lyznik et al. 1996) and *Zygosaccharomyces rouxii* (R—RS). In each of these systems, no additional factor aside from the recombinase and target sequences is required for recombination. Reviewed in van Haaren and Ow, 1993. The CRE-loxP site-specific recombination system of bacteriophage P1 has been studied extensively in vitro and in *E. coli* (Craig 1988; Adams et al. 1992). Expression of the CRE protein (38.5 kDa) is sufficient to cause recombination between 34 bp loxP sites that consist of 13 bp inverted repeats separated by 8 bp asymmetric spacer sequence. If there are two loxP sites within a DNA segment, the result of the recombination reaction depends on the relative position of the recombination sites. If the recombination sites form a direct repeat, that if they are in the same orientation, recombination results in deletion of the intervening DNA. If the recombination sites are in an inverted orientation, CRE-mediated recombination results in an inversion of the intervening DNA. The products of these reactions are shown in FIG. 1. The CRE site-specific recombination system has been employed for the elimination of nuclear genes in a number of eukaryotic systems, including higher plants (Dale and Ow 1991; Russell et al. 1992; Srivastava et al. 1999).

Before the present invention, the efficiency of CRE-mediated elimination of targeted plastid genes was unknown. To explore this system for this purpose, CRE-mediated elimination of the codA gene encoding cytosine deaminase (CD; EC 3.5.4.1) was assessed. Cytosine deaminase converts 5-fluorocytosine (5FC) into 5-fluorouracil (5FU), the precursor of 5-fluoro-dUMP. 5FC is lethal for CD-expressing cells due to irreversible inhibition of thymidylate synthase by 5-fluoro-dUMP (Beck et al. 1972). Cytosine deaminase is absent in plants. Expression of the bacterial coda in plastids renders cells sensitive to 5FC, while cells deficient in transgene expression are resistant (Serino and Maliga 1997). Thus, 5FC resistance could be used for positive identification of cells with CRE-induced coda deletion, even if such deletion events were relatively rare. The test system of the present invention incorporates a coda gene in the tobacco plastid genome between two directly oriented lox sites (>codA>). The transplastome was stable in the absence of CRE activity. However, highly efficient elimination of >codA> was triggered by introduction of a nuclear-encoded plastid-targeted CRE.

EXAMPLE 1

Cre-Mediated Deletion of the Selectable Plastid Marker

Cre-mediated deletion of the selective plastid marker in the plastids of tobacco somatic cell is described in Example I. The selectable marker flanked by the lox sites is exemplified here by coda. However, it could be any other selectable and non-selectable marker gene, or any DNA sequence independent of information content flanked by lox sites in the plastid genome. Components of the test system are tobacco plants carrying a coda coding region flanked by lox sites (>codA>). A second component of the test system is a nuclear gene encoding a plastid targeted CRE-site specific recombinase. Deletion of a plastid encoded >codA> is achieved by introducing nuclear Cre into the nucleus of somatic (leaf) tobacco cells by *Agrobacterium*-mediated transformation. Alternatively, the nuclear encoded Cre gene may be introduced by fertilization with pollen of an appropriate activator-of-deletion strain. The nuclear Cre gene is subsequently removed by segregation in the seed progeny.

Materials and Methods for the Practice of Example 1

The following materials and methods are provided to facilitate the practice of Example 1.

Plastid codA with direct lox sites.

Figure 2:
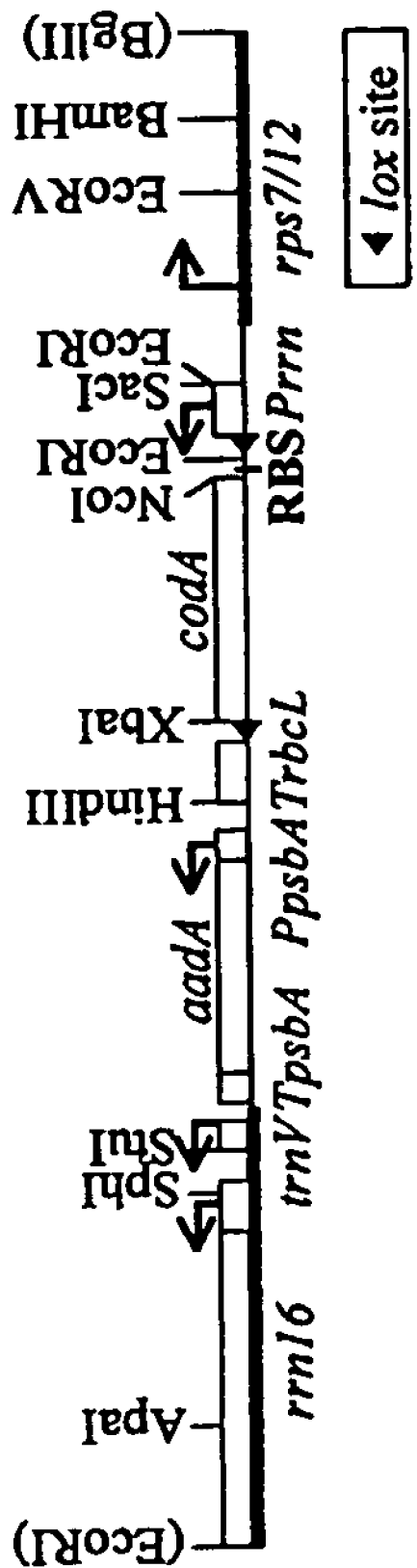
FIG. 2 is a map of a plastid transformation vector pSAC48, with coda bracketed by direct loxP sites. Positions of plastid genes rrn16, trnV, rps12/7 (Shinozaki et al. 1986), the aadA and codA transgenes and relevant restriction sites are marked.

The codA gene is contained in a SacI-HindIII fragment. The gene map is shown in FIG. 2. PrrnloxD (Seq. ID No. 4) is a plastid rRNA operon (rrn16) promoter derivative. It is contained in a SacI-EcoRI fragment obtained by PCR using oligonucleotides 5'-GGGGAGCTCGCTCCCCCGC-CGTCGTTCAATG-3' (SEQ ID NO: 14) and 5'-GGGAAT-TCATAACTTCGTATAGCATACATTATACGAAGTTAT GCTCCCAGAAATATAGCCA-3' (SEQ ID NO: 15) as primers and plasmid pZS176 (progenitor of plasmid pZS197; Svab and Maliga 1993) as a template. The promoter fragment PrrnloxD contains a lox site at the 3' end adjacent to the EcoRI site. The EcoRI-NcoI fragment contains the ribosome binding site from plasmid pZS176. The fragment was obtained by annealing the complementary oligonucleotides 5'-AATTCGAAGCGCTTGGATAC AGT-TGTAGGGAGGGATC-3' (SEQ ID NO: 16) and 5'-CATG-GATCCCTCCCTACAACTGTATCCAAGCGCTTCG-3' (SEQ ID NO: 17). The codA coding region is contained in an NcoI-XbaI fragment (Serino and Maliga 1997). The TrbcLloxD (Seq. ID No. 5) is the rbcL 3'-untranslated region contained in an XbaI-HindIII fragment obtained by PCR using oligonucleotides 5'-GGTCTAGATAACTTCG-TATAATGTATGCTATACGAAGTTATAGACAT TAGCA-GATAAATT-3' (SEQ ID NO: 18) and 5'-GGGGGTAC-CAAGCTTGCTAGATTTTGTATTTCAAATCTTG-3' (SEQ ID NO: 19) and plasmid pMSK48 (Khan and Maliga 1999) as template. TrbcLloxD contains a lox site adjacent to the XbaI site in direct orientation relative to the lox site in the codA 5'UTR. The chimeric PrrnloxD:codA:TrbcLloxD gene was introduced into the tobacco plastid transformation vector pPRV111B (Zoubenko et al. 1994) as a SacI-HindIII fragment to obtain plasmid pSAC48.

Figure 3:
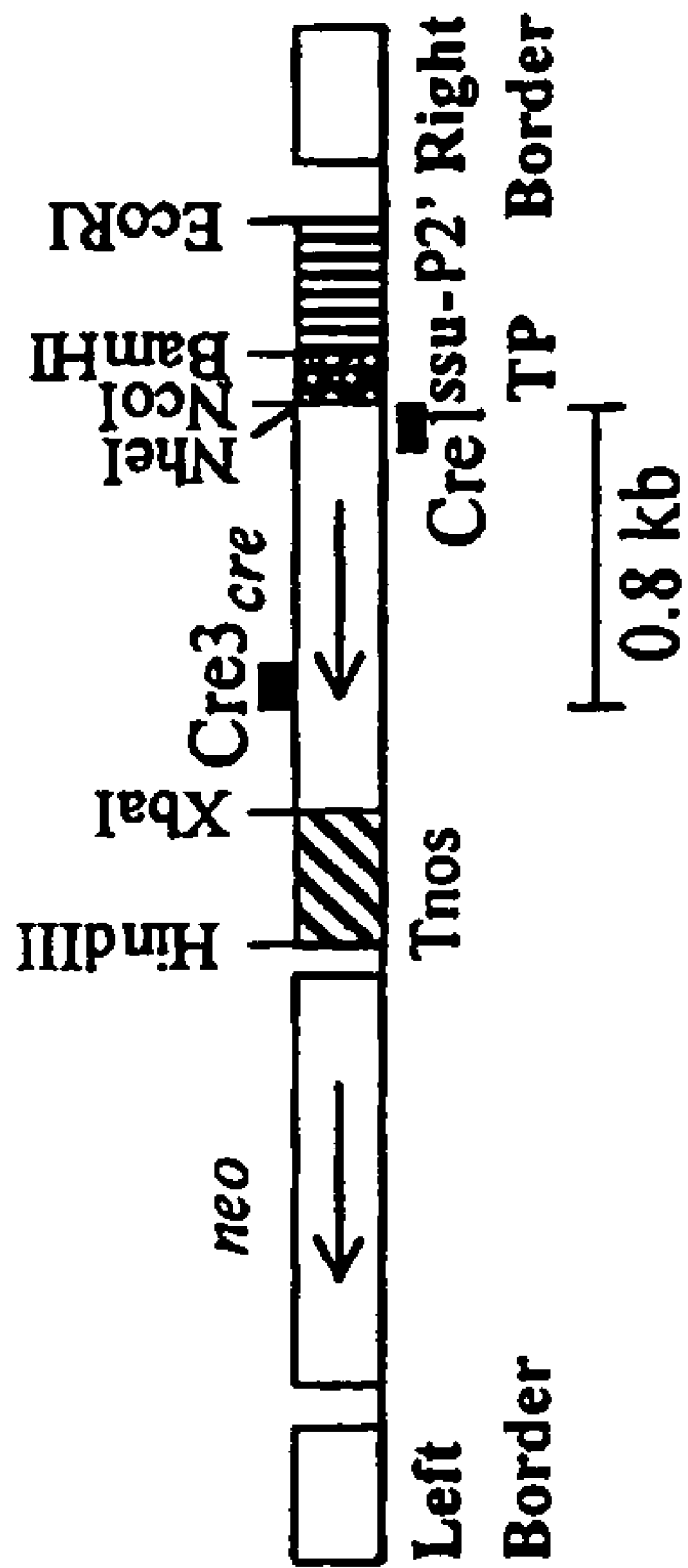
FIG. 3 is a map of an *Agrobacterium* binary vector pPZP212 with a plastid-targeted Ssu-tp-cre gene. Marked are: *Agrobacterium* Left and Right Border fragments; the kanamycin resistance (neo) gene; P2' promoter; SSU transit peptide (ssu-tp); cre coding region; recognition sequences for restriction enzymes BamHI, EcoRI, HindIII, NcoI, NheI and XbaI.

Plastid-targeted nuclear cre linked to a nuclear kanamycin resistance gene. Two plastid targeted nuclear cre genes were tested. The cre gene in *Agrobacterium* binary vector pKO27 and pKO28 encode the CRE recombinase at its N terminus translationally fused with the pea Rubisco small subunit (SSU) chloroplast transit peptide (Timko et al. 1985) and twenty two and five amino acids of the mature Rubisco small subunit, respectively. Both cre genes are contained in an EcoRI-HindIII fragment. The schematic map of the genes is shown in FIG. 3. The P2' *Agrobacterium* promoter (Velten et al. 1984) (Sequence ID. No.9) is contained in an EcoRI-NcoI fragment. The P2' promoter fragment was obtained by PCR using oligonucleotides 5'-ccgaattcCATTTTCACGTGTGGAAGATATG-3' SEQ ID NO: 20) and 5'-ccccatggtaggatcctatCGATTTGGTGTATCGAGATTGG-3' (SEQ ID NO: 21) as primers and plasmid pHC1 (Carrer et al. 1990) as template. PCR amplification introduced an EcoRI site at the 5' end and ClaI, BamHI and a NcoI sites at the 3=end. A T introduced between the ClaI and the BamHI sites eliminates an ATG and introduces an in-frame stop codon (Sriraman 2000). The Rubisco SSU transit peptides are included in BamHI-NcoI fragments. The pKO27 fragment (Pea SSU-TP22; Sequence ID No. 7) was obtained by using oligonucleotides 5'-CCGGATCCAATTCAACCACAAGAAC-TAAC-3' (SEQ ID NO: 22) and 5'-GGGGCTAGCCATGGCAGGCCACACCTG-CATGCAC-3' (SEQ ID NO: 23) as primers and plasmid pSSUpGEM4 as the template (Timko et al. 1985). The pKO28 fragment (Pea SSU-TP5; Sequence ID No. 6) was obtained by using oligonucleotides 5'-CCGGATCCAAT-TCAACCACAAGAACTAAC-3' (SEQ ID NO: 22) and 5'-GGGGCTAGCCATGGTCAATGGGTTCAAATAGG-3' (SEQ ID NO: 24) as primers and plasmid pSSUpGEM4 as the template (Timko et al. 1985). The cre coding region included in a NcoI-XbaI fragment (Sequence ID No. 3) was obtained by PCR amplification using the Cre1 5'-GGG-GAGCTCCATGGCTAGCTCCAATTTACT-GACCGTACAC-3' (SEQ ID NO: 25) and Cre2 5'-GGGTCTAGACTAATCGCCATCCTCGAG-CAGGCGCACCATTGC-3' (SEQ ID NO: 26) oligonucleotides as primers and DNA isolated from *Escherichia coli* strain BNN132 (ATCC number 47059) as template. The presence of cre gene in plant nuclear DNA was confirmed by PCR amplification with the Cre 1 and Cre3 oligonucleotides. The sequence of Cre3 oligonucleotide is 5'-TCAATCGAT-GAGTTGCTTC-3' (SEQ ID NO:27). The *Agrobacterium* nos terminator (Tnos) is included in a XbaI-HindIII fragment (Svab et al. 1990). The plastid targeted nuclear cre genes were introduced as EcoRI-HindIII fragments into the pPZP212 *Agrobacterium* binary vectors (Hajdukiewicz et al. 1994) to obtain plasmids pKO27 and pKO28 with twenty two and five amino acids of the mature Rubisco SSU. A schematic map of the *Agrobacterium* vectors is shown in FIG. 3.

Transgenic plants. Plastid transformation using the biolistic protocol, selection of transplastomic tobacco clones (RMOP medium, 500 mg/L spectinomycin dihydrochloride) and characterization of the transplastomic clones by DNA gel blot analysis was described (Svab and Maliga 1993). Transformation with *Agrobacterium* vectors pKO28 or pKO27 and regeneration of transformed tobacco plants has also been reported (Hajdukiewicz et al. 1994). Briefly, nuclear gene transformants were selected by kanamycin resistance on RMOP shoot regeneration medium containing 100 mg/L kanamycin and 500 mg/L carbenicillin. Kanamycin resistance of the shoots was confirmed by rooting on plant maintenance (RM) medium containing 100 mg/L kanamycin. Testing of 5FC cytotoxicity was carried out on RMPO medium according to published procedures (Serino and Maliga 1997).

Transplastomic tobacco plants with a codA gene flanked by direct lox sites.

Plastid transformation vector pSAC48 carries a codA gene in which two lox sites flank the coding region in a direct orientation. If the codA coding region is deleted via the lox sites, a lox site flanked by the promoter (Prrn) and terminator (TrbcL) are left behind. The selective marker in pSAC48, a pPRV111B vector derivative, is a spectinomycin resistance (aadA) gene (FIG. 2). Transformation with plasmid pSCAC48 yielded a number of independently transformed transplastomic lines, of which four were purified to the homoplastomic state: Nt-pSAC48-21A, Nt-pSAC48-16C, Nt-pSAC48-16CS and Nt-pSAC48-9A. These lines are considered identical other than they have been generated independently. A uniform population of transformed plastid genomes in the transplastomic plants was verified by DNA gel blot analysis (see below).

Nuclear-encoded plastid-targeted Cre genes.

To activate deletion of the plastid >codA> gene we introduced an engineered cre gene into the nucleus of the transplastomic lines encoding a plastid-targeted CRE. Targeting of nuclear-encoded plastid proteins is by an N-terminal transit peptide (TP) cleaved off during import from the cytoplasm into plastids (Soll and Tien, 1998). To ensure plastid targeting of the CRE recombinase, it was translationally fused with the Rubisco small subunit (SSU) transit peptide (Timko et al. 1985). Therefore, the product of the protein fusion is SSU-TP-CRE. Efficiency of import of chimeric proteins depends on the size of mature protein N-terminus incorporated in the construct (Wasmann et al. 1986; Lubben et al. 1989). Two chimeric cre genes (Ssu-tp-cre) were prepared, one with 5 (vector pKO28) and one with 22 (plasmid pKO27) amino acids of the mature SSU N-terminus, encoding SSU-TP5-CRE and SSU-TP22-CRE, respectively. These genes are also referred to as Cre1 and Cre2, respectively (Table 1). The cre genes were expressed in the P2' promoter and Tnos terminator cassettes in the *Agrobacterium* pPZP212 binary vector which carries kanamycin resistance (neo) as a selectable marker (FIG. 3).

Tobacco plant transformed with Ssu-tp5-cre (pKO37) and Ssu-tp22-cre (pKO36) were also obtained. In these plants the nuclear cre is expressed from the cauliflower mosaic virus 35S promoter (Seq. ID No. 10; Timmermans et al. 1990).

| Line | Plastid genotype[a] | Nuclear marker |
|---|---|---|
| Wild-type | trnV+ aadA− codA− | |
| Nt-pSAC48-21A | trnV+ aadA+ codA+ | |
| Nt-pSAC48-16C | | |
| Cre1-1 | trnV+ aadA+ codA− | neo |
| | trnV− aadA− codA− | |
| Cre1-2 | trnV+ aadA+ codA− | neo |
| | trnV− aadA− codA− | |
| Cre1-3 | trnV+ aadA− codA− | neo |
| Cre1-4 | trnV− aadA− codA− | neo |
| Cre1-10 | trnV− aadA− codA− | neo |
| Cre2-1 | trnV+ aadA+ codA− | neo |
| Cre2-2 | trnV+ aadA+ codA− | neo |
| | trnV+ aadA*+ codA− | |
| | trnV− aadA− codA− | |
| Cre2-3 | trnV+ aadA+ codA+ | neo |
| | trnV+ aadA+ codA− | |
| | trnV+ aadA*+ codA− | |
| | trnV− aadA− codA− | |
| Cre2-4 | trnV+ aadA+ codA− | neo |

-continued

| Line | Plastid genotype[a] | Nuclear marker |
|---|---|---|
| Cre2-5 | trnV+ aadA+ codA− | neo |
| Cre2-10 | trnV+ aadA+ codA−<br>trnV− aadA− codA− | neo |
| Cre1-100 | trnV+ aadA− codA− | neo |
| Cre2-100 | trnV+ aadA− codA− | neo |
| Cre2-200 | trnV+ aadA− codA− | neo |
| Cre2-300 | trnV+ aadA− codA− | neo |

[a]Presence or absence of plastid gene is indicated by + or −. Since the plastid trnV gene is deleted in some of the lines, the wild-type plastid genotype is trnV+ aadA− codA−.

Deletion of coda from the plastid genome in somatic cells.

Figure 4:
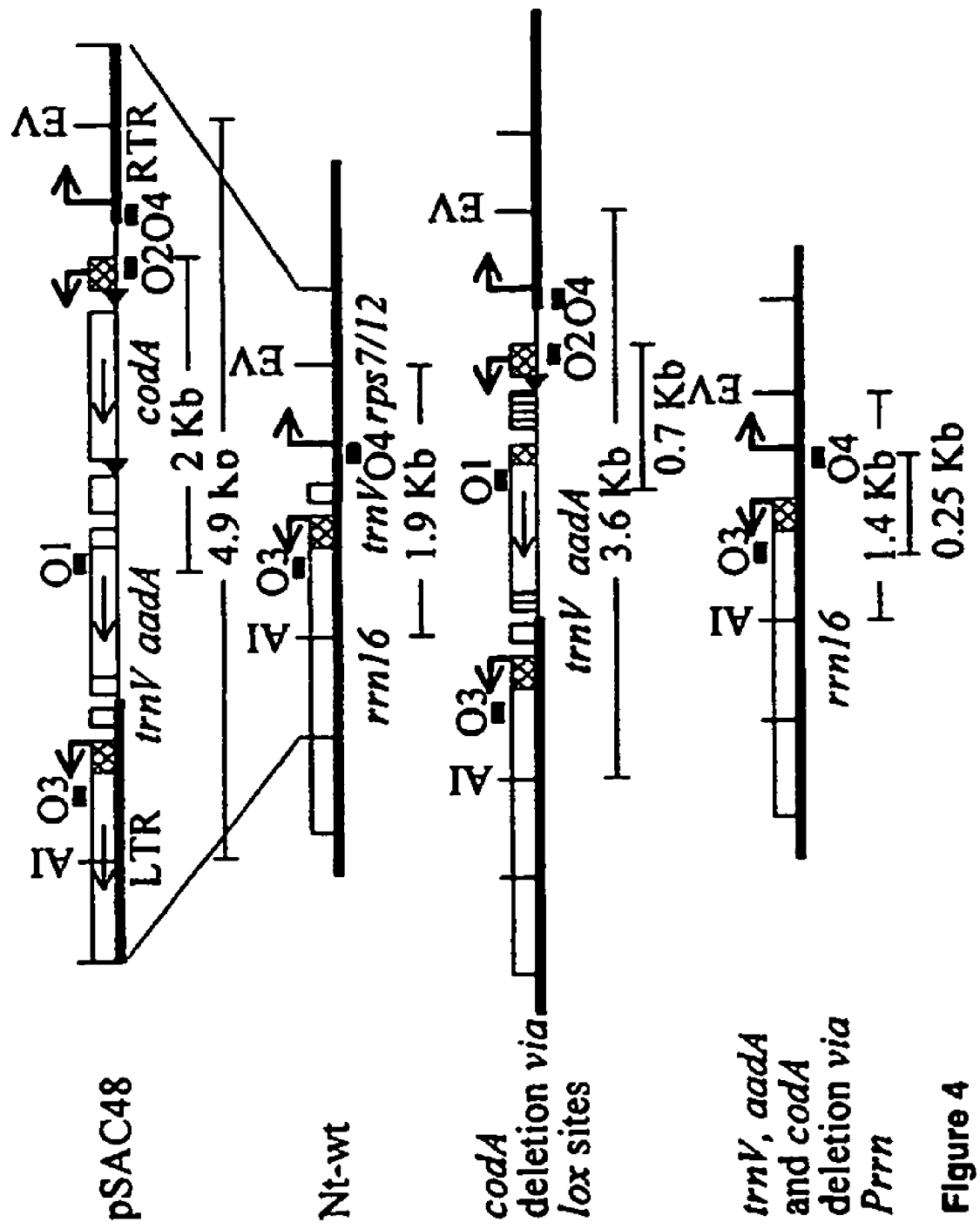
FIG. 4 shows maps of the plastid genome >codA> deletion derivatives. Shown are the plastid targeting region of vector pSAC48; the map of same region of the wild-type plastid genome (Nt-wt); the map of the plastid genome with CRE-mediated deletion of coda via the lox sites; and the map of the plastid genome with deletion via Prrn sequences lacking trnV, aadA and coda. Positions of plastid genes rrn16, trnV and rps12/7 (Shinozaki et al. 1986), aadA and codA transgenes, primers (O1–O4) and relevant restriction sites (AI, ApaI; EV, EcoRV) are marked.
Figure 5:
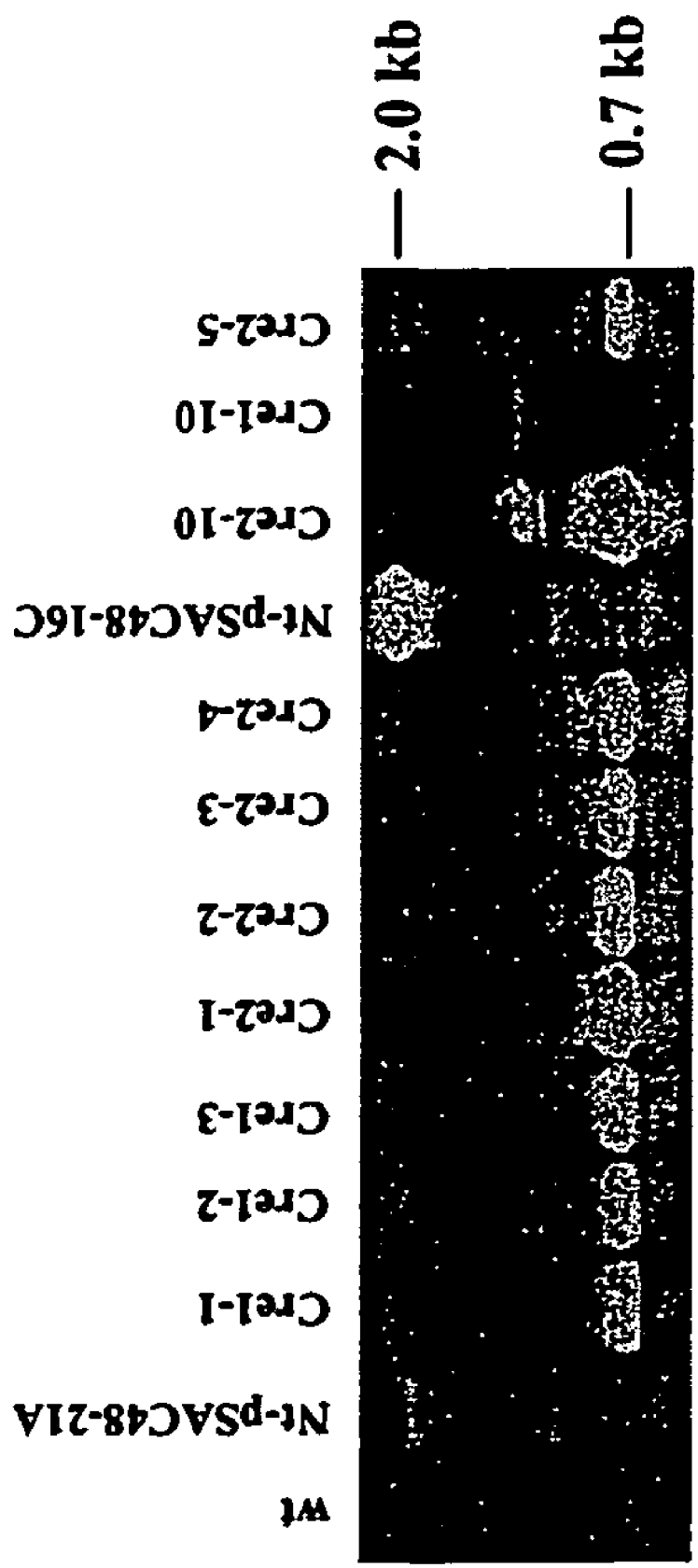
FIG. 5 is a gel showing PCR amplification which confirms CRE-mediated deletion of codA from the plastid genome. Primers O1 and O2 (FIG. 3) amplified the 0.7-kb fragment of the deleted region. Same primers amplify the 2.0-kb aadA-codA fragment in tester lines Nt-pSAC48-21A and Nt-pSAC-16C (no transgenic Cre gene). No specific fragment was obtained in wild-type DNA sample and in Cre1-10 line. The lines obtained are listed in Table 1.
Figure 6:
FIG. 6 shows the results of DNA gel blot analysis wherein plastid genome structure was determined in the indicated plant samples. Total cellular DNA was isolated from the leaves of plants listed in Table 1 and digested with the ApaI and EcoRV restriction endonucleases. The probes were the wild-type ApaI-EcoRV plastid targeting region and the aadA (NcoI-XbaI fragment) and coda (NcoI-XbaI fragment) coding regions. The hybridizing fragments are marked in FIG. 3.
Figure 7:
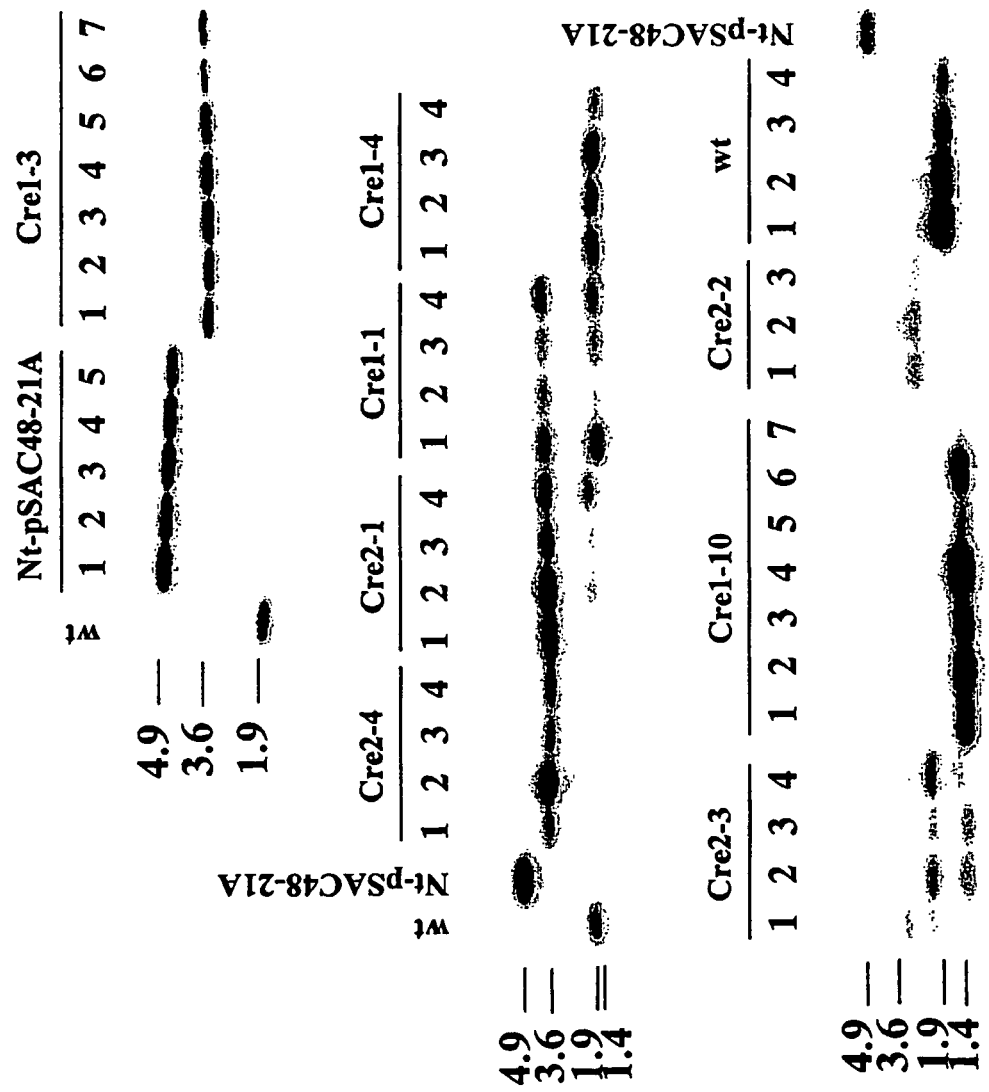
FIG. 7 are gels showing uniformity of plastid genome populations in the Ssu-tp-cre transformed plants. Total cellular DNA extracted from several leaves was probed with the ApaI-EcoRV targeting region probe. Numbers identify leaves from which DNA was extracted. For example, seven different leaves were probed from the Cre1-3 plant. For details, see Brief Description of FIG. 6.

To test the efficiency of CRE-mediated deletion in somatic cells, the Ssu-tp-cre genes were introduced into the nucleus of the transplastomic >codA> lines by cocultivation of *Agrobacterium* and tobacco leaf disks. Plants representing 11 individual Ssu-tp-cre insertion events have been characterized. Five lines (Cre1-derivatives) were obtained by transformation with Ssu-tp5-cre gene (vector pKO28) and six lines (Cre2-derivatives) were obtained by transformation with the Ssu-tp22-cre (vector pKO27) (Table 1). Deletion of coda was first tested in a DNA sample taken from one leaf of eleven kanamycin resistant shoots representing an individual integration event of the nuclear Cre gene. Subsequently, 4 to 7 additional leaves were sampled from six shoots to confirm that the result of the analysis is typical for the plant. The initial DNA samples were first screened for the loss of >codA> by PCR using the O1/O2 primer pair complementary to sequences in the aadA coding region N terminus and the coda promoter (FIG. 4A). Amplification with these primers yields a ~0.7-kb fragment if >codA> is deleted and a ~2.0-kb fragment if the >codA> gene is still present. Ethidium bromide stained gels of PCR products in FIG. 5 indicate complete loss of >codA> in each of the samples. A perfect, reconstituted lox site between Prrn and TrbcL was confirmed in eight clones by PCR amplification of the region with primers O1/O4 from the same DNA samples and direct sequencing of the amplification product with primer $O_2$ (not shown). In two clones (Cre1-4, Cre1-10) a fragment is missing due to deletion of aadA alongside with coda (see below). Plastid genome structure in the initial DNA sample was determined by gel blot analysis of ApaI-EcoRV digested total cellular DNA. The probes were the plastid targeting region and the aadA and coda coding regions. The DNA gel blots are shown in FIG. 6. The maps of the parental genomes and deletion derivatives that help to interpret these genomes are shown in FIG. 4. In the plastid tester strains expressing no CRE (Nt-pSAC48-21A, Nt-pSAC48-16C) all three probes hybridized to the same 4.9-kb DNA fragment consistent with both coda and aadA being present in all the plastid genome copies. In the SSU-TP-CRE expressing plants no 4.9-kb fragment was detectable indicating the dramatic speed by which the >codA> gene was eliminated from the plastid genome. CRE-mediated deletion of >codA> via the lox sites yielded the 3.6-kb fragment detected in nine of the eleven clones. The 3.6-kb fragment was the only product detected in four clones, and was present in a heteroplastomic population in five clones. Unanticipated was formation of a 1.4-kb ApaI-EcoRV fragment in five clones. DNA gel blot analysis confirmed that this fragment lacks both coda and aadA, and is smaller than the wild type ApaI-EcoRV fragment (1.9-kb). Direct sequencing of PCR products in this region confirmed deletion of coda, aadA and trnV by homologous recombination via the duplicated Prrn promoter regions. One of the Prrn promoters is driving codA, the other is upstream of the rRNA operon at its native location. Deletion of trnV is the reason why the ApaI-EcoRV fragment derived from this region (1.4-kb) is smaller than the wild-type fragment (1.9-kb). The initial DNA samples were taken from one leaf of a plant obtained by rooting the shoot obtained after transformation with the Ssu-tp-cre genes. To confirm that the DNA samples extracted from the leaf were typical for the plant, we have sampled several more leaves from the same plants (FIG. 7). In four clones coda was excised by CRE via the lox sites, and the shoots were homoplastomic for the deleted genome. Two of these, Cre1-3 and Cre2-4 were further characterized by testing seven and four additional leaves of the same plants, respectively. DNA gel blot analysis of these samples confirmed a uniform deletion of >codA> from all genome copies. These plants are the desired final products carrying the desired plastid transgenes and lacking the undesirable selective marker. These plants and their progeny can be used directly for the production of recombinant proteins as they are free from the selectable marker gene. Furthermore, these plants are a source of engineered chloroplasts for introduction into breeding lines by sexual crossing. The seed progeny of the plants is segregating for the Ssu-tp-cre activator gene. Plants with the desired chloroplasts but lacking the activator gene can be identified by PCR testing for cre sequences. Alternatively, individuals lacking cre can be identified in the seed progeny by sensitivity to kanamycin, since the Ssu-tp-cre genes in the pKO27 and pKO28 *Agrobacterium* vectors are physically linked to kanamycin resistance (neo gene; FIG. 3). In two clones, Cre1-4 and Cre1-10, deletion of trnV (encoding tRNA-Val$^{GAC}$), aadA and codA occurred by homologous recombination via the duplicated Prrn promoter region. The Cre1-10 plant is homoplastomic for the deletion based on probing seven additional leaves (FIG. 7). Apparently, the one remaining trnV gene encoding tRNA-Val$^{UAC}$ is sufficient for the translation of all valine codons, or there is import of tRNA-Val$^{GAC}$ from the cytoplasm. In the Cre1-4 clone some of the leaves (two out of four) contained residual genome copies with trnV and aadA.

In five clones the initial DNA samples contained more than one type of plastid genome copies. Mixed populations of plastid genome populations were confirmed in all parts of the plants by testing additional leaves (FIG. 7). Genetically stable coda deletion lines can be obtained from these heteroplastomic plants by testing plants regenerated from single somatic cells or individual seedlings in a segregating seed progeny.

Deletion of coda from the plastid genome in the seed progeny.

CRE-mediate deletion of the negative plastid marker coda in somatic cells was described in the previous section. Deletion of the plastid marker gene in the somatic cells of the transplastomic plants, without going though a sexual cycle, is highly desirable to accelerate the production of marker-free transplastomic plants. However, this approach is feasible only if there is a system for tissue culture and plant regeneration from somatic cells. Such system is unavailable for the economically important cereal crops rice and maize. As an alternative to transformation of somatic cells, we developed CRE activator lines carrying a nuclear-encoded plastid-targeted Cre to be used as the source of Cre gene when used as a pollen parent. The tobacco CRE activator lines were obtained by transforming the nucleus of wild-type plants with SSU-TP-CRE constructs. Lines in which the Cre is linked to a nuclear kanamycin resistance gene in a wild-type cytoplasm are Cre1-100, Cre-2-100, Cre2-200 and Cre2-300 (Table 1). To activate deletion of >codA> in the seed progeny, tester plants Nt-pSAC48-21A and Nt-pSAC48-16C were emasculated to prevent self fertilization, and fertilized with pollen from the Cre2-200 and Cre2-300 activator lines. The activator lines are primary transgenic plants ($T_0$) segregating for the Ssu-tp-cre gene. Therefore, a proportion of the seed progeny derived from the cross will have the activator genes while others will not. If the coda gene is present, the O1/O2 primer pair marked in FIG. 4 amplifies a 2.0-kb fragment. If the coda gene is absent, the same primers will amplify a 0.7-kb fragment. PCR analysis shown in FIG. 8 confirmed CRE-mediated deletion of >codA> in seedlings. The Cre1-100, Cre2-100 and Cre2-300 activator lines are apparently expressing CRE efficiently, indicated by the presence of only of the 0.7-kb fragment in seedlings carrying the nuclear cre gene. In seedlings with no cre sequence the same primers amplified the 2.0-kb coda-containing fragment. Interestingly, cre+ seedlings from the cross with Cre2-200 contained a mixed population of coda containing (2.0-kb) and coda-deleted (0.7-kb) fragments indicating less efficient CRE-induced deletion of >codA>. Thus, expression level and tissue specificity of the two nuclear Ssu-tp22-cre genes are characteristic for the individual transformation events. CRE activity of Cre1-100, Cre2-100 and Cre2-300 activator lines is more suitable for rapid elimination of >codA> in a cross than the Cre2-200 line. It is undesirable to maintain the Ssu-tp-cre activator genes in the production lines. However, these are encoded in the nucleus, and can be separated from the transgenic chloroplasts in the next seed progeny. Linkage of Ssu-tp-cre to the nuclear kanamycin resistance gene facilitates identification of seedlings lacking cre in a segregating seed population.

CRE site-specific recombinase for deletion of plastid DNA sequences. Biolistic transformation of tobacco leaves always yields shoots containing a mixed population of plastid genome copies. A mixed population of plastid genome copies is determined by DNA gel blot analysis (Carrer et al. 1993; Svab and Maliga 1993; Carrer and Maliga 1995) and can be visualized in UV light when expressing the green fluorescence protein in plastids (Khan and Maliga 1999). Homoplastomic, genetically stable plants are obtained during a second cycle of plant regeneration from the leaves of the regenerated plants or in the seed progeny. The cells of the >codA> tester strains carry a uniform population of plastid genome copies. Thus, the Ssu-tp-cre is introduced into the nuclear genome of a cell that is homoplastomic for >codA>. It was expected that the regenerated shoots would contain a mixed population of plastid genome copies. Instead, all plastid genome copies lack >codA>, an evidence for the enormous selection pressure by CRE activity against plastid genome copies that carry two lox sites. It is important that deletion of >codA> occurs in the absence of selection against >codA> by exposure to 5-fluorocytosine. Virtually complete elimination of >codA> may also be obtained when CRE activity is introduced by crossing, using pollen of an appropriate deletion activator strain. Deletion of the selectable marker in somatic cells is the preferred choice over elimination of the marker in the seed progeny. The most important advantage is time saving. Introduction of Ssu-tp-cre into the nucleus of somatic cells requires only three to six weeks; Ssu-tp-cre segregates out in the first seed progeny. In contrast, introduction and elimination of Ssu-tp-cre takes one additional seed progeny, about three months.

Interestingly, genome copies with one lox site or no lox site (wild-type) are stable in CRE-expressing cells. Instability of genomes with two lox sites may be due to formation of linear ends during the excision process. The linear ends may then re-circularize by homologous recombination via the Prrn promoter sequences yielding the trnV-aadA-codA deletion derivatives.

CRE engineering. Although CRE is a prokaryotic protein, it naturally carries a nuclear localization signal (NLS) that targeted a CRE-GFP fusion protein to the nucleus in mammalian cells. The NLS sequences overlap the DNA binding regions and the integrity of this region is important for DNA recombinase activity (Le et al. 1999). We targeted the newly-synthesized TP-CRE protein to plastids using a plastid-targeting transit peptide (TP). The TP is localized at the N terminus of plastid proteins and is cleaved off during import from the cytoplasm into plastids (Soll and Tien, 1998). Therefore, we translationally fused a plastid transit peptide with CRE to direct its import from the cytoplasm to plastids. Translational fusion yielded a protein with an N-terminal plastid targeting signal and an internal nuclear localization signal. Efficient CRE-mediated deletion of plastid-encoded coda genes indicates targeting of SSU-TP-CRE to plastids. When two potential targeting sequences are present, in general one of them out-competes the other (Small et al. 1998). N-terminal organelle targeting sequences normally dominate the second internal localization signal. For example, the 70-kDa heat shock protein of watermelon cotyledons that carry N-terminal plastidal and internal glyoxysomal targeting sequences are exclusively targeted to plastids. Proteins are localized to glyoxysomes only in the absence of the plastidal presequence (Wimmer et al. 1997). The tRNA modification enzymes contain information for both mitochondrial (N-terminal extension) and nuclear targeting. The enzyme with the N-terminal extension is targeted to mitochondria and only the short form lacking the N-terminal extension is targeted to the nucleus (Small et al. 1998). It was fortunate, that the Rubisco SSU N-terminal transit peptide dominated the CRE nuclear localization signals and the TP-CRE fusion protein was directed to plastids (chloroplasts). A second property that is important for the present invention is maintenance of recombinase activity when CRE is fused with proteins or peptides at its N and C termini. N-terminal fusion of CRE with the *E. coli* maltose binding protein did not interfere with recombinase function (Kolb and Siddell 1996). CRE was also shown to accept a C-terminal fusion with GFP (Le et al. 1999) as well as an 11-amino-acid epitope to the herpes simplex virus (HSV) glycoprotein D coat protein. The epitope tag facilitates detection of CRE expression in vitro and in vivo using immunofluorescent labeling with a commercially available antibody (Stricklett et al. 1998). Apparently, the five and 22 amino acids that are left behind after processing of the SSU-TP5-CRE and SU-TP22-CRE proteins did not interfere with CRE function.

Dominant negative selection markers for positive identification of deletion derivatives. A practical application of the present invention is the removal of selectable marker genes from the transformed plastid genome. In tobacco, the excision process mediated by the CRE constructs described herein is so efficient that the >codA> deletion derivatives can be identified in the absence of 5FC selection. However, in other crops CRE-mediated excision of marker genes may be less efficient. In these species, the positive selective marker (aadA) may be fused with a dominant negative selective marker using linker peptides as described in the literature (Khan and Maliga 1999) or the positive and negative marker genes may be combined in a dicistronic operon (Staub and Maliga 1995). Dominant negative selection markers allow normally non-toxic compounds to be used as toxic agents, so that cells which express these markers are non-viable in the presence of the compound, while cells that don't carry them are unaffected. For example, cytosine deaminase is absent in plants. Expression of coda, encoding cytosine deaminase (CD; EC 3.5.4.1), in plastids renders tissue culture cells and seedlings sensitive to 5FC, facilitating direct identification of clones lacking this negative selective marker (Serino and Maliga 1997). Cytosine deaminase converts 5-fluorocytosine (5FC) into 5-fluorouracil (5FU), the precursor of 5-fluoro-dUMP. 5FC is lethal for CD-expressing cells due to irreversible inhibition of thymidylate synthase by 5-fluoro-dUMP (Beck et al. 1972). We have found that seedlings and plant tissues expressing >codA> were sensitive to 5FC. Seedlings lacking coda could be readily identified by 5FC resistance. Thus, the constructs described here are suitable to express cytosine deaminase at sufficiently high levels to be useful to implement a negative selection scheme.

Alternative negative selective markers can be obtained by adaptation of substrate-dependent negative selection schemes described for nuclear genes. Such negative selection schemes are based on resistance to indole, napthyl, or naphtalene acetamide (Depicker et al. 1988; Karlin-Neumann et al. 1991; Sundaresan et al. 1995), chlorate (Nussaume et al. 1991), kanamycin (Xiang and Guerra 1993) and 5-fluorocytosine (5FC) (Perera et al. 1993; Stougaard 1993).

EXAMPLE 2

Cr-Mediated Inversion of Plastid DNA Sequences

Figure 9:
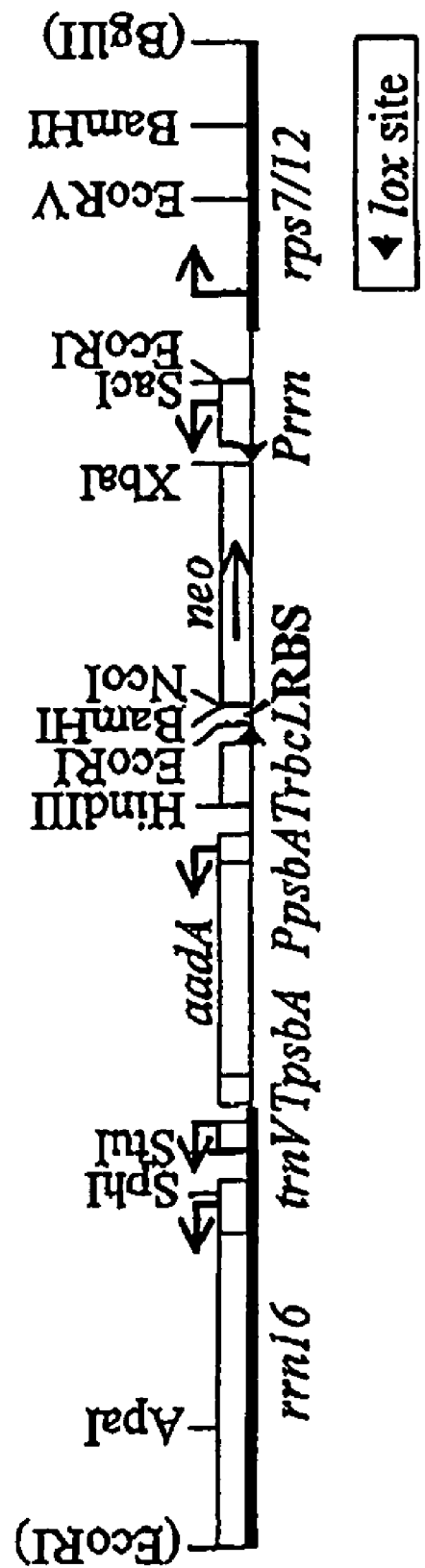
FIG. 9 is a diagram of the plastid transformation pSAC38 with the >neo< bracketed by inverted lox sites. Positions of plastid genes rrn16, trnV and rps12/7 (Shinozaki et al., 1986), the aadA and codA transgenes and relevant restriction sites are marked.

If the lox sites in bacteria are in an inverted orientation, CRE-mediated recombination results in an inversion of the intervening DNA. We have tested, whether the CRE-mediated inversion reaction also occurs in plastids of higher plants containing DNA sequences flanked by inverted lox sites. This was assessed using a kanamycin-resistance (>neo<) coding region in an inverted orientation relative to the promoter (FIG. 9). In this construct the non-coding strand of neo is transcribed and the plants are kanamycin sensitive. The >neo< coding region is flanked by inverted lox sites. CRE-mediated inversion of the sequences reverses neo orientation resulting in the transcription of the sense strand and expression of kanamycin resistance. Inversion of the plastid-encoded >neo< coding region may be achieved by multiple approaches. One approach is to introduce a nuclear Cre into the nucleus of somatic tobacco cells, e.g., leaf, by Agrobacterium-mediated transformation. A second approach is introduction of the nuclear-encoded Cre gene by fertilization with pollen of an appropriate activator-of-inversion strain. Additional approaches are to provide CRE-activity via the incorporation of chemically inducible promoter into the construct, or to transiently express CRE from a nuclear of chloroplast construct.

Materials and Methods for the Practice of Example 2

Figure 8:
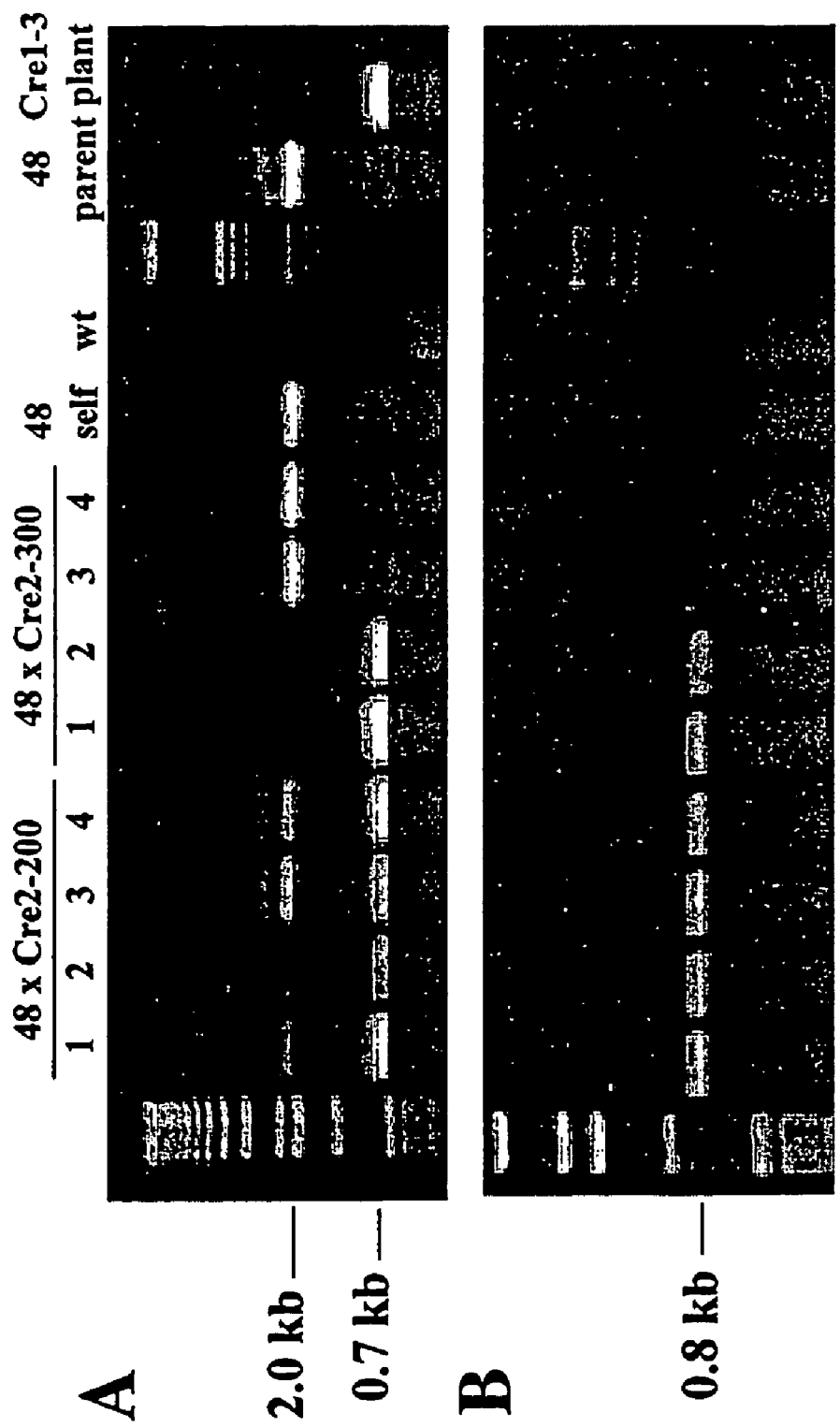
FIGS. 8A and 8B are gels of PCR analysis confirming CRE-mediated deletion of coda in seedlings obtained by pollination with Ssu-tp-cre activator lines. 5-day old seedlings were tested from the cross Nt-pSAC48-21A as maternal parent and Cre2-200 and Cre2-300 activator lines as pollen parents. Amplification products are also shown for controls Nt-pSAC48-21A selfed seedling (48 self), wild-type (wt), the parental plant (48P) and the Cre1-3 plant.

Plastid neo gene with inverted lox sites. The neo gene is contained in a SacI-HindIII fragment. The gene map is shown in FIG. 8. PrrnloxI (Seq. ID No. 1) is a plastid rRNA operon (rrn16) promoter derivative. It is contained in a SacI-XbaI fragment obtained by PCR using oligonucleotides 5'-ggggagctcGCTCCCCCGCCGTCGTTCAATG-3' (SEQ ID NO: 14) and 5'-gg tctagataacttcgtatagcatacattatacgaagttatGCTCCC AGAAATATAGCCA-3' (SEQ ID NO: 28) as primers and plasmid pZS176 (progenitor of plasmid pZS197; Svab and Maliga 1993) as a template. The promoter fragment PrrnloxI contains a lox site at the 3' end adjacent to the XbaI site. The neo coding region is contained in an NcoI-XbaI fragment derived from plasmid pHC62. The neo sequence in plasmid pHC62 is identical with the neo sequence shown in FIG. 28B, U.S. Pat. No. 5,877,402. The EcoRI-NcoI fragment contains the ribosome binding site from plasmid pZS176. The fragment was obtained by annealing the complementary oligonucleotides 5'-AATTCGAAGCGCTTGGATACAGT-TGTAGGGAGGGATC-3' (SEQ ID NO: 16) and 5'-CATG-GATCCCTCCCTACAACTGTATCCAAGCGCTTCG-3' (SEQ ID NO: 17). The TrbcLloxI (Seq. ID No. 2) is the rbcL 3'-untranslated region contained in an EcoRI-HindIII fragment obtained by PCR using oligonucleotides 5'-gg gaattcataacttcgtatagcatacattatac gaagttatAGACATTAGCA-GATAAATT-3'(SEQ ID NO: 29) and 5'-gg gggtaccaagcttgCTAGATTTTGTATTTCAAATCTTG-3' (SEQ ID NO: 19) and plasmid pMSK48 (Khan and Maliga 1999) as template. TrbcLloxI contains a lox site adjacent to the EcoRI site in an inverted orientation relative to the lox site in PrrnloxI. The chimeric PrrnloxI:neo:TrbcLloxI gene was introduced into the tobacco plastid transformation vector pPRV111B (Zoubenko et al. 1994)

Plastid-targeted nuclear cre linked to a nuclear gentamycin resistance (aacC1) gene. The plastid targeted nuclear cre genes were introduced as EcoRI-HindIII fragments into the pPZP222 Agrobacterium binary vectors which carry a plant-selectable gentamycin resistance gene (Hajdukiewicz et al. 1994) to obtain plasmids pKO30 and pKO31 with twenty two and five amino acids of the mature Rubisco SSU. The map of the Agrobacterium vectors is identical with the one shown in FIG. 3. other than they carry a gentamycin resistance gene.

Transplastomic tobacco plants with a neo gene flanked by inverted lox sites.

Plastid transformation vector pSAC38 with the inverted >neo< gene is shown in FIG. 9. The inverted >neo< gene was introduced into plastids by selection for spectinomcyin resistance (aadA) encoded in the vector. Two independently transformed lines were purified to the homoplastomic state: Nt-pSAC38-9A and Nt-pSAC38-10C. The homoplastomic state was confirmed by DNA gel blot analysis.

Nuclear-encoded plastid-targeted Cre genes.
Plant activator lines in which Ssu-tp-cre is linked to a nuclear kanamycin resistance gene have been described in Example 1. The plastid marker to test CRE-activated inversion described in Example 2 utilizes a kanamycin resistance gene. Kanamycin resistance conferred by the plastid gene due to CRE-mediated inversion could not be distinguished from kanamycin resistance conferred by the marker gene of the Agrobacterium binary vector that was used to introduce the nuclear cre. Therefore, we have constructed activator strains in which Ssu-tp-cre is linked to gentamycin resistance. The Ssu-tp22-cre gene linked to the nuclear gentamycin resistance is the Cre3 strain and the Ssu-tp5-cre gene linked to gentamycin resistance is the Cre4 strain.

Figure 10:
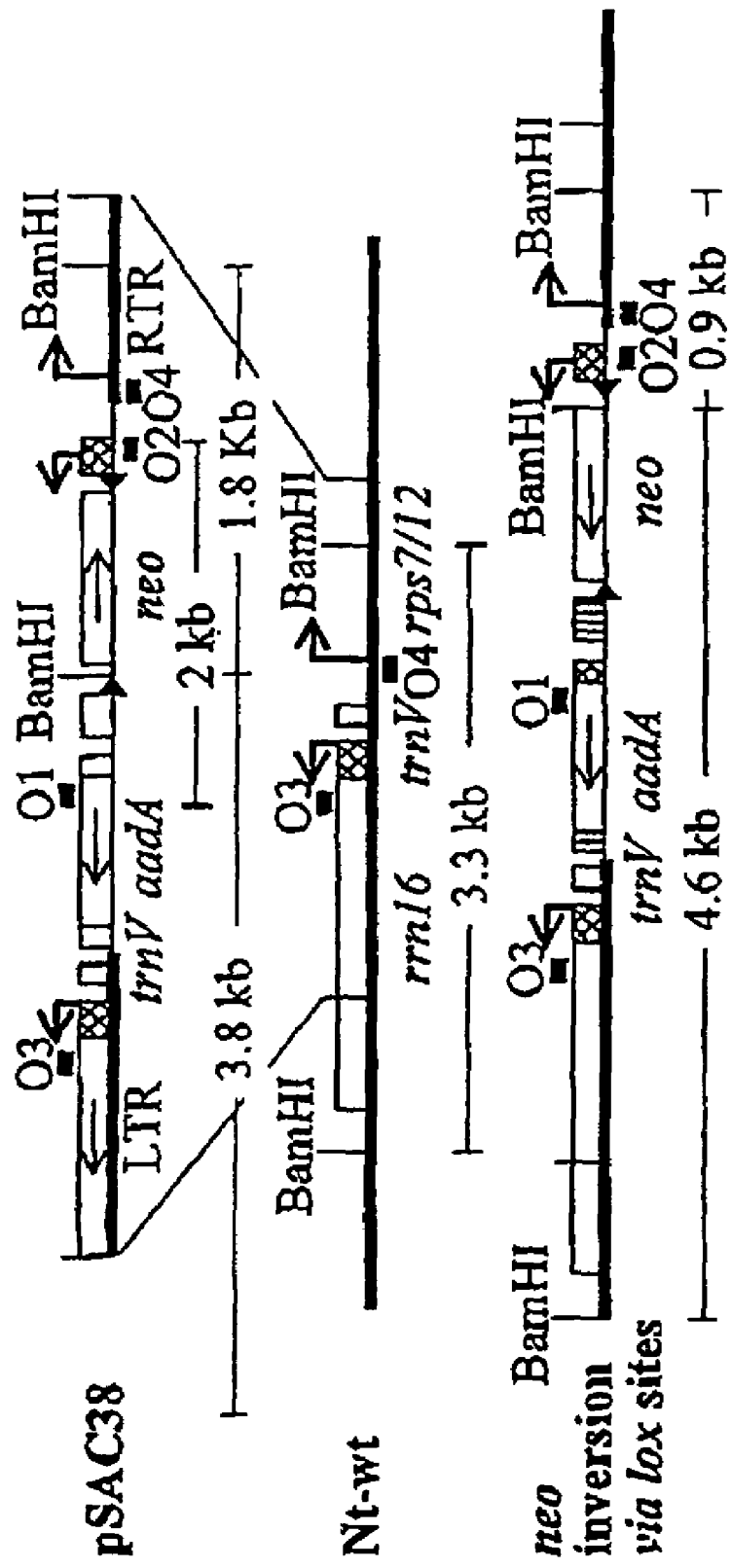
FIG. 10 shows a map of the plastid genome containing the >neo< inversion construct. Shown are the plastid targeting region of vector pSAC38; the map of the same region of the wild-type plastid genome (Nt-wt); map of the plastid genome with CRE-mediated inversion of neo via the lox sites. Positions of the plastid genes rrn16, trnV and rps12/7 (Shinozaki et al., 1986) aadA and neo transgenes, primers (O1–O4) and relevant restriction sites (BamHI) are marked.
Figure 11:
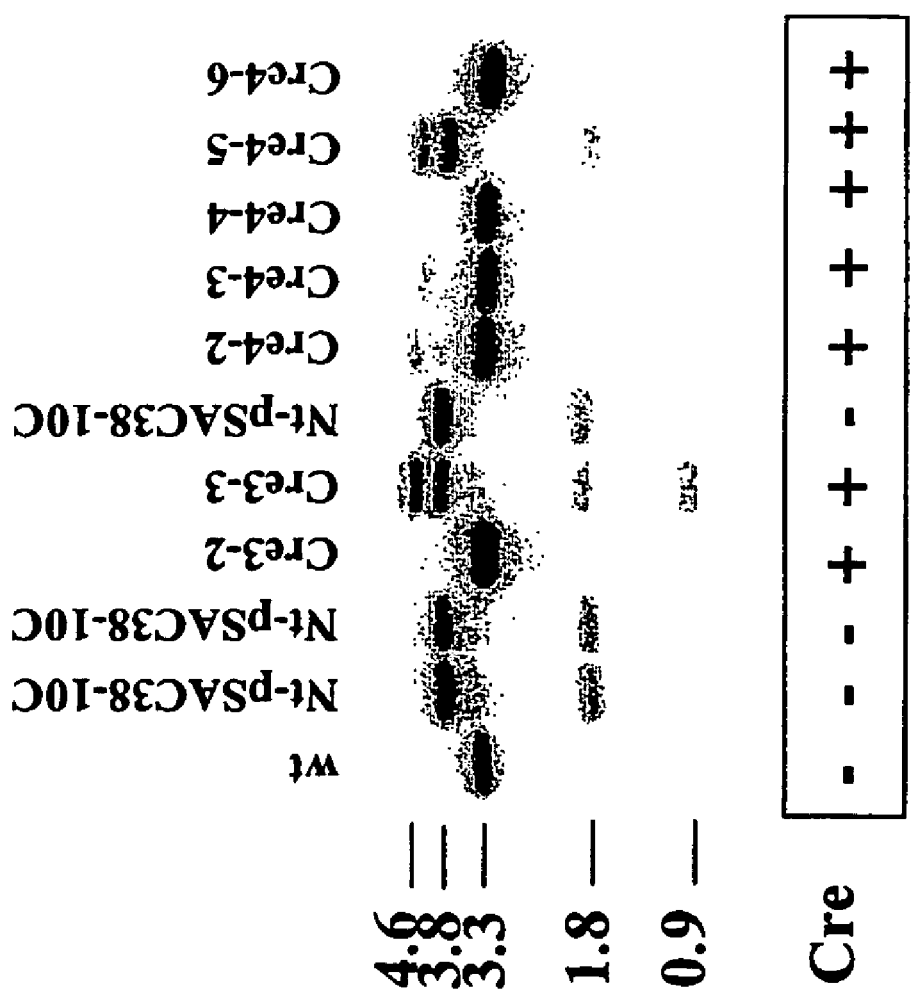
FIG. 11 shows the results of DNA gel blot analysis for the determination of plastid genome structure of CRE-activated >neo< plants by DNA gel blot analysis. Total cellular DNA was digested with the BamHI restriction endonuclease. The probes was the wild-type ApaI-EcoRV plastid targeting region. The hybridizing fragments are marked in FIG. 10.

Inversion of >neo< in the plastid genome of somatic cells.
The nuclear cre genes were introduced into the chloroplast >neo< tester strains by cocultivation of tobacco leaves with the *Agrobacterium* strains and selection for gentamycin resistance (100 mg/L). Digestion of total cellular DNA with BamHI and probing with the plastid targeting region (ApaI-EcoRV fragment, FIG. 4) hybridizes to 1.8-kb and a 3.8-kb fragments in the parental Nt-pSAC38-10C lines (FIG. 10). Activation by CRE in lines Cre3-3 and Cre4-5 created a mixed population of >neo< genes representing the original and inverted orientations detected as the original 3.8-kb and 1.8-kb and the newly created 4.6-kb and 0.9-kb hybridizing fragments. Lines carrying the cre and an approximately wild-type size fragment are aadA-neo deletion derivatives, similar to those shown in FIG. 4. Thus, it appears that CRE mediated inversion via lox sites creates increased local recombination frequencies that leads to deletion of the transgenes via the short direct repeats of Prrn promoters.

Controlling inversion via lox sites by CRE activity.

Here we describe constructs for CRE-mediated inversion of plastid genome segments flanked by inverted lox sites. Inversion of the sequences is independent of the encoded genetic information and relies only on CRE activity. CRE activity may be provided transiently, by expression in plastids from plastid signals described in U.S. Pat. No. 5,877,402, or from nuclear genes encoding a plastid-targeted CRE. Such plastid-targeted CRE constructs are described in Example 1, for example the Ssu-tp5-cre or Sssu-tp22-cre genes. Alternative approaches to provide CRE activity are stable incorporation of a plastid-targeted nuclear Cre into the nucleus of somatic (leaf) cells by *Agrobacterium*-mediated, PEG induced or biolistic transformation or by fertilization with pollen from a transformed plant. The *Agrobacterium* P2 promoter and cauliflower mosaic virus 35S promoter exemplified here are constitutive promoters. Regulated expression of CRE may be important for certain applications. Developmentally timed expression may be obtained from promoters with tissue specific activity. Regulated expression of CRE may be obtained from chemically induced nuclear gene promoters responding to elicitors, steroids, copper or tetracycline (reviewed in; Gatz et al. 1992; Mett et al. 1993; Aoyama and Chau 1997; Gatz 1997; Martinez et al. 1999; Love et al. 2000) and described in U.S. Pat. No. 5,614,395.

Controlled Expression of Deleterious Gene Products

There are a variety of valuable heterologous proteins that interfere with plastid metabolism. For example, certain proteins may be inserted into photosynthetic membranes and interfere with photosynthesis. This problem can be circumvented by first growing the plants to maturity, then activating production of the deleterious protein by chemically inducing CRE expression. CRE, in turn, will make the gene expressible by lox-mediated inversion of the coding region.

Figure 12:
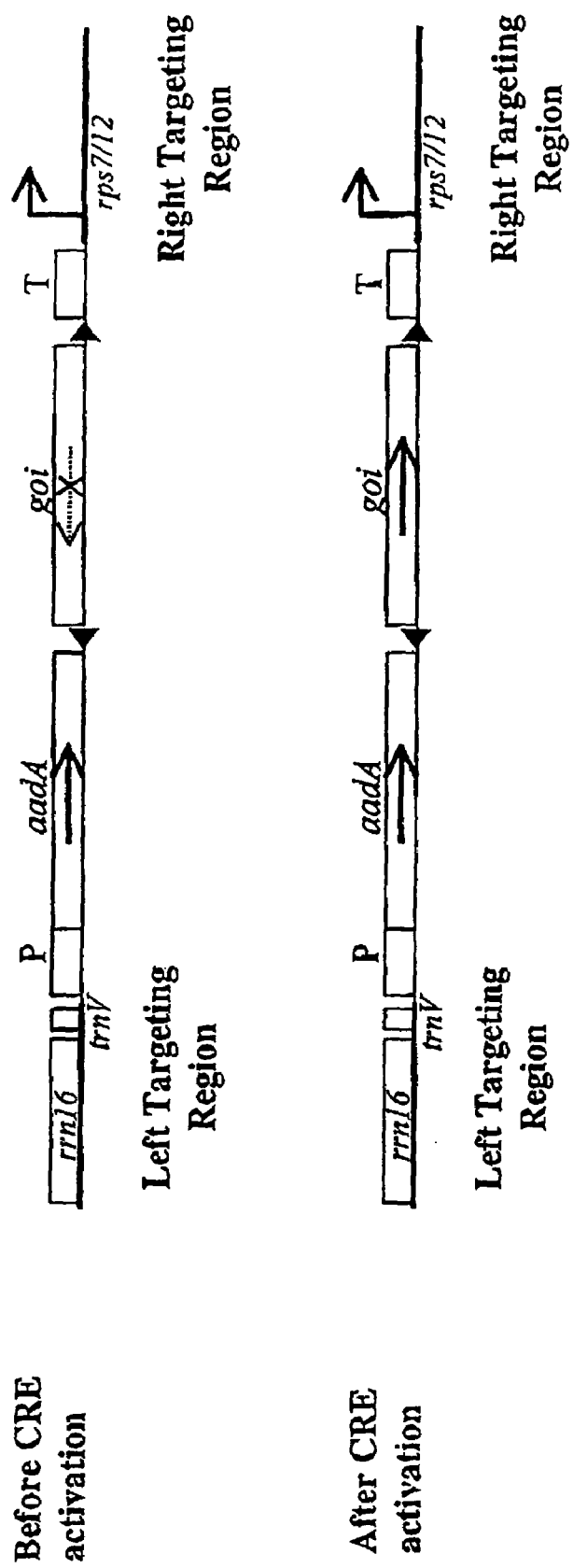
FIG. 12 shows an exemplary monocistronic inversion vector. The gene of interest (goi) coding region is flanked by inverted lox sites (triangles). CRE activates goi expression by inversion, so that the coding strand is transcribed. rrn16, trnV and rps12/7 are plastid genes (Shinozaki et al. 1986).

The molecular tools necessary for the construction of such plastid genes are described in present application. In case of the monocistronic inversion vector the gene of interest (goi) is flanked by inverted lox sites and is introduced by linkage with aadA (FIG. 12). The selectable marker (aadA) coding region is the first reading frame, and is expressed from the promoter. The goi reading frame is the second coding region, and it is not expressed as it is in an inverted orientation relative to the promoter. Expression of goi is induced by CRE-mediated inversion of the goi coding region, as described for >neo< in Example 2 and is shown in FIG. 12.

Figure 13:
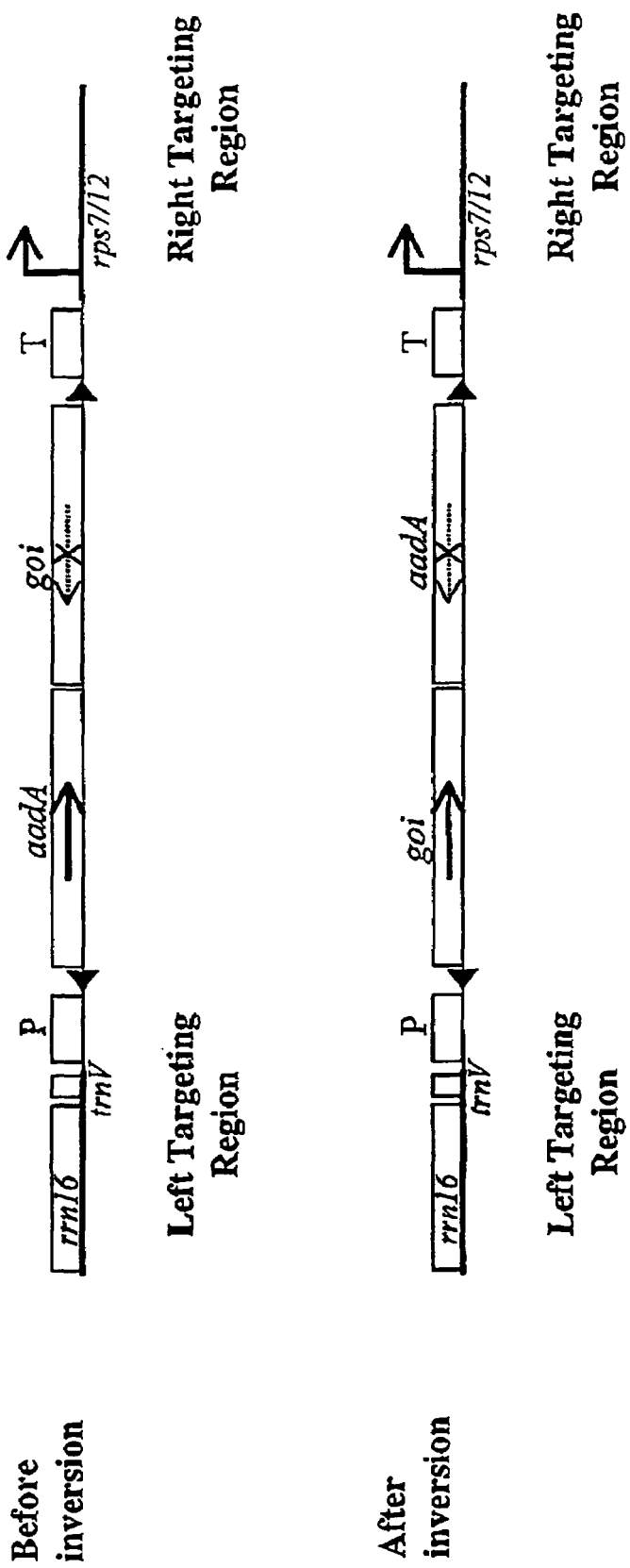
FIG. 13 shows an alternative dicistronic lox inversion vector. Note that the inverted lox sites flank the selective marker (aadA) and goi, and only one gene is expressed. rrn16, trnV and rps12/7 are plastid genes (Shinozaki et al. 1986).

The dicistronic lox inversion vector is shown in FIG. 13. In this case the inverted lox sites flank both aadA and goi. The selectable marker (aadA) coding region is expressed from the promoter. The goi reading frame is not expressed as it is in an inverted orientation relative to the promoter. Expression of goi is induced by CRE-mediated inversion of the aadA-goi containing region that results in simultaneous expression of goi and inactivation of aadA.

The presence of two lox sites may destabilize the plastid genome that leads to CRE-independent deletion of plastid genome sequences. However, it appears that CRE activity by itself is not mutagenic, and the plastid genomes are stable if only one lox site is present. Mutant lox sites that are efficiently excised but recombine into excision resistant sites have been described (Hoess et al. 1982; Albert et al. 1995). Such lox sites would mediate efficient inversion, but the new lox sites would be resistant to additional cycles of CRE activation. Providing only a short burst of CRE activation using a chemically induced promoter could further refine the expression system.

EXAMPLE 3

CRE-Mediated Deletion to Obtain Marker Free Transplastomic Plants and for High Level Expression of the Recombinant Proteins Plastid loxP vectors in this section are described for CRE-mediated excision of selective markers in transplastomic plants. Since excision of sequences between directly oriented lox sites is very efficient, variants of the same vectors can be used for CRE-activated expression of recombinant proteins. A family of plastid vectors with suitably positioned lox sites is shown schematically in FIG. 14 through FIG. 17.

Figure 14:
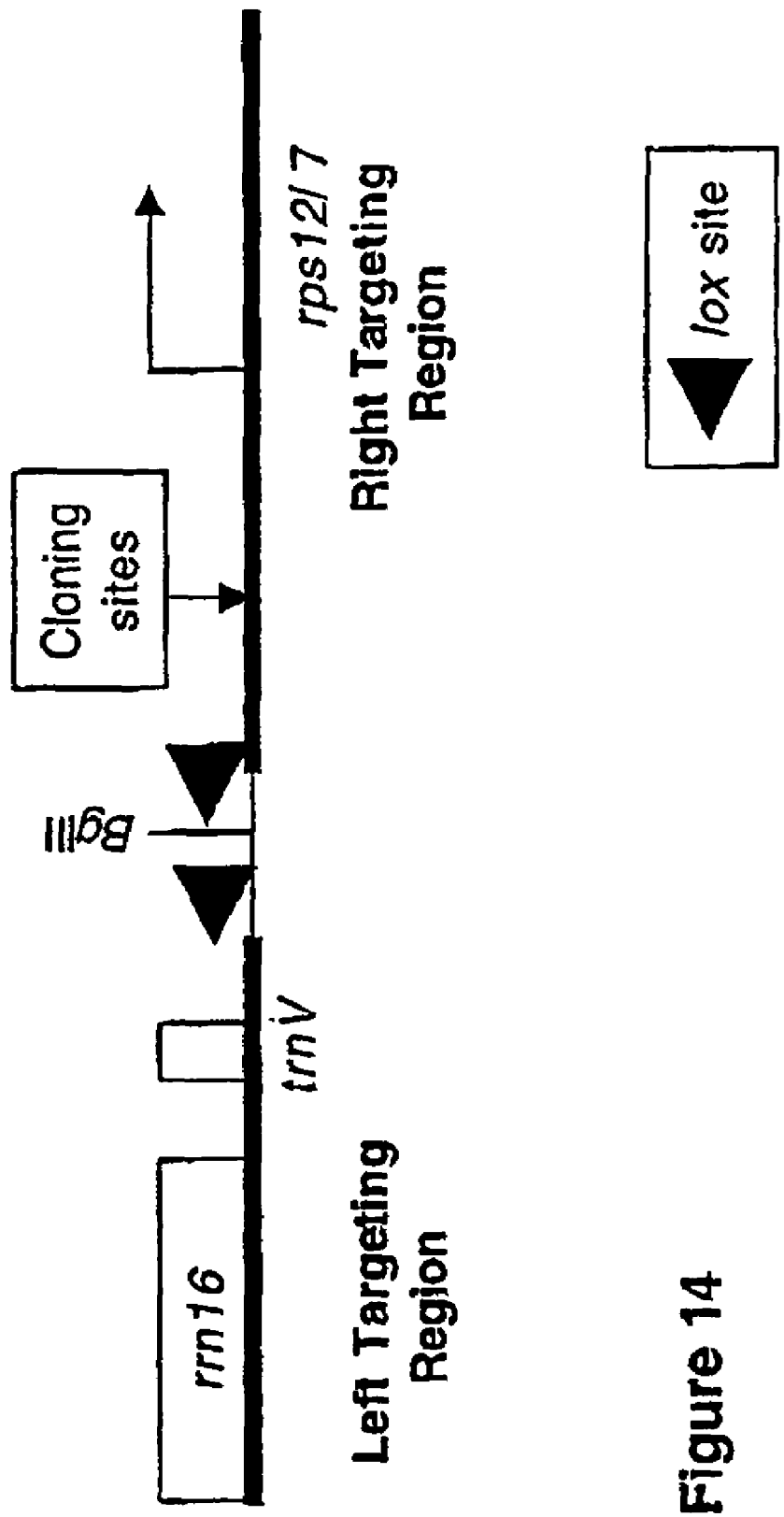
FIG. 14 shows a basic tobacco plastid lox deletion vector. The vector provides is a suitable backbone for vector construction and targets insertions into the trnV-rps12/7 intergenic region.

The map of the basic tobacco plastid lox deletion vector is shown in FIG. 14. It contains (a) two directly oriented lox sites separated by a unique BglII cloning site and (b) an adjacent polycloning site. These sequences (Seq. ID No. 11) are inserted into the ScaI site plastid repeat vector pPRV100 (U.S. Pat. No. 5,877,402; Zoubenko et al. 1994). Suitable marker genes (aadA, neo or kan, bar, glyphosate resistance, bromoxynil resistance) for insertion into the BglII site have been described in U.S. Pat. No. 5,877,402, WO 00/07421 and WO 00/03022.

Figure 15:
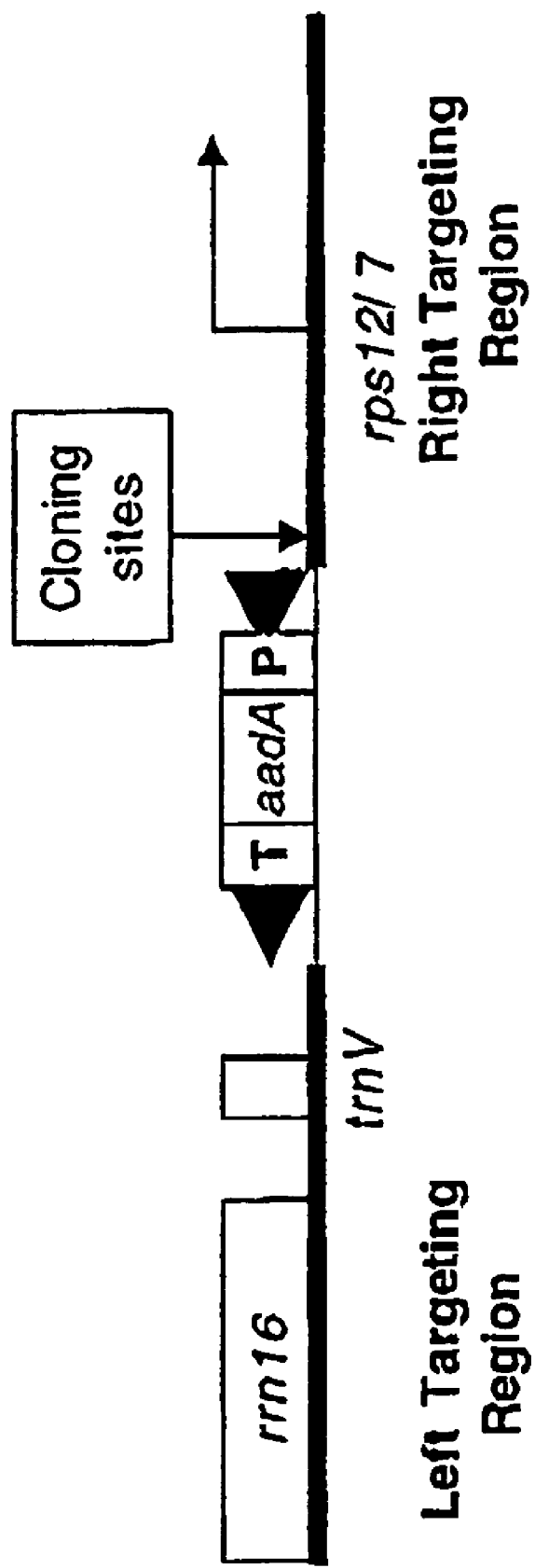
FIG. 15 shows a tobacco plastid lox >aadA> deletion vector. rrn16, trnV and rps12/7 are plastid genes (Shinozaki et al. 1986).

The map of the tobacco plastid lox >aadA> deletion vector is shown in FIG. 15. It is the basic lox deletion vector with an aadA gene cloned into the BglII sites oriented towards the rrn operon.

Figure 16:
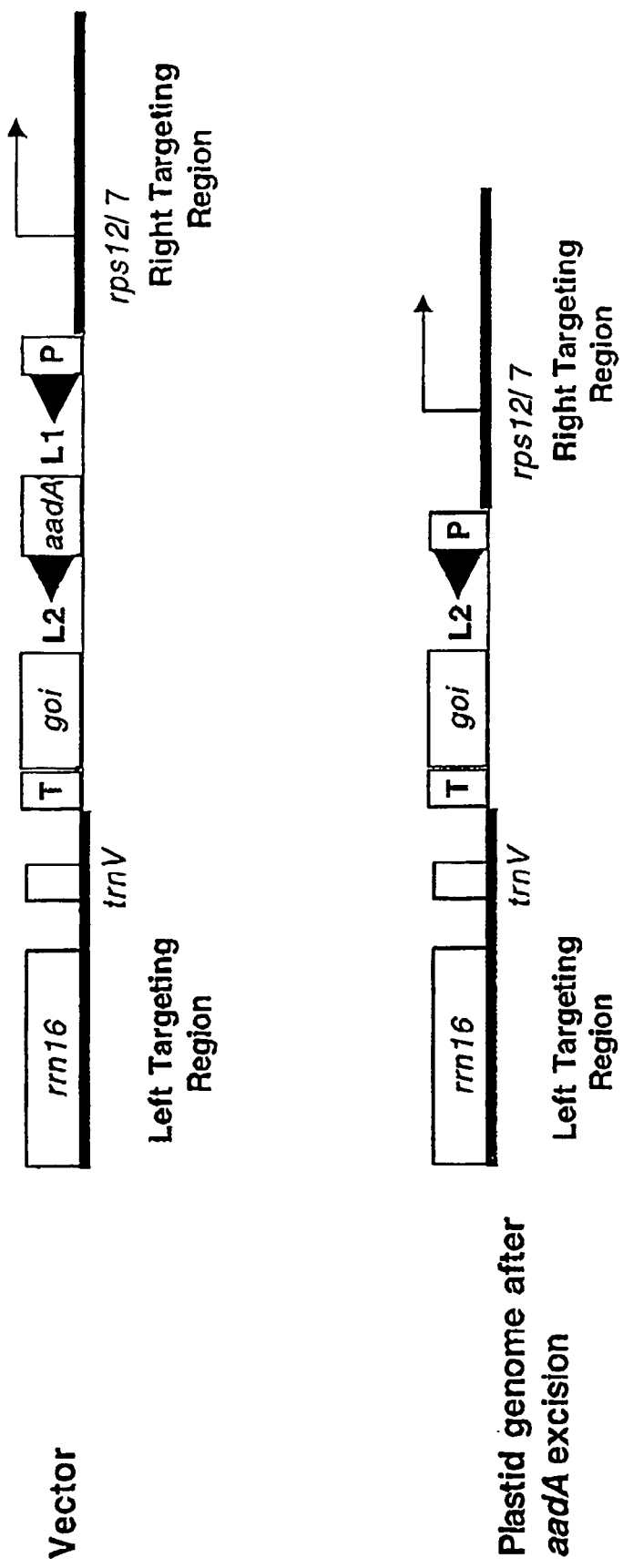
FIG. 16 shows a tobacco constitutive >aadA> goi dicistronic deletion vector. rrn16, trnV and rps12/7 are plastid genes and are described in (Shinozaki et al. 1986).
Figure 17:
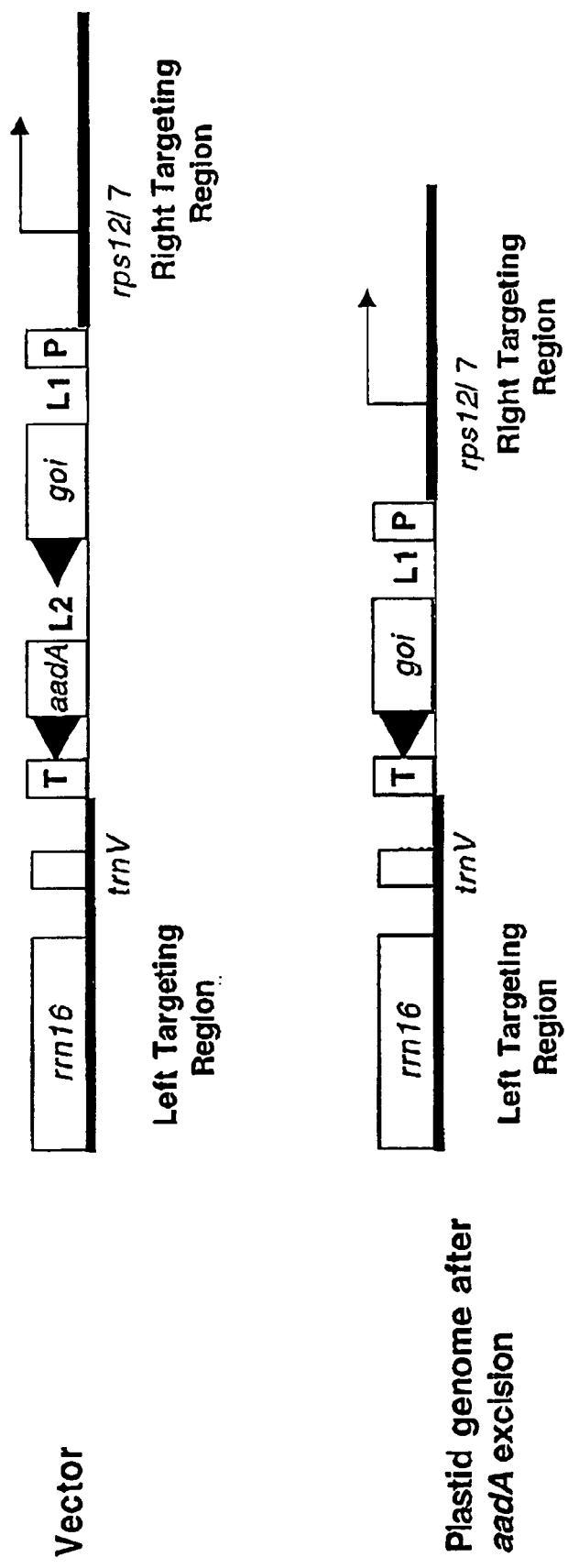
FIG. 17 shows a tobacco constitutive goi >aadA> dicistronic deletion vector. Note that vectors shown in FIG. 16 and FIG. 17 differ in the relative order of marker gene and the gene of interest. rrn16, trnV and rps12/7 are plastid genes (Shinozaki et al. 1986).
Figure 18:
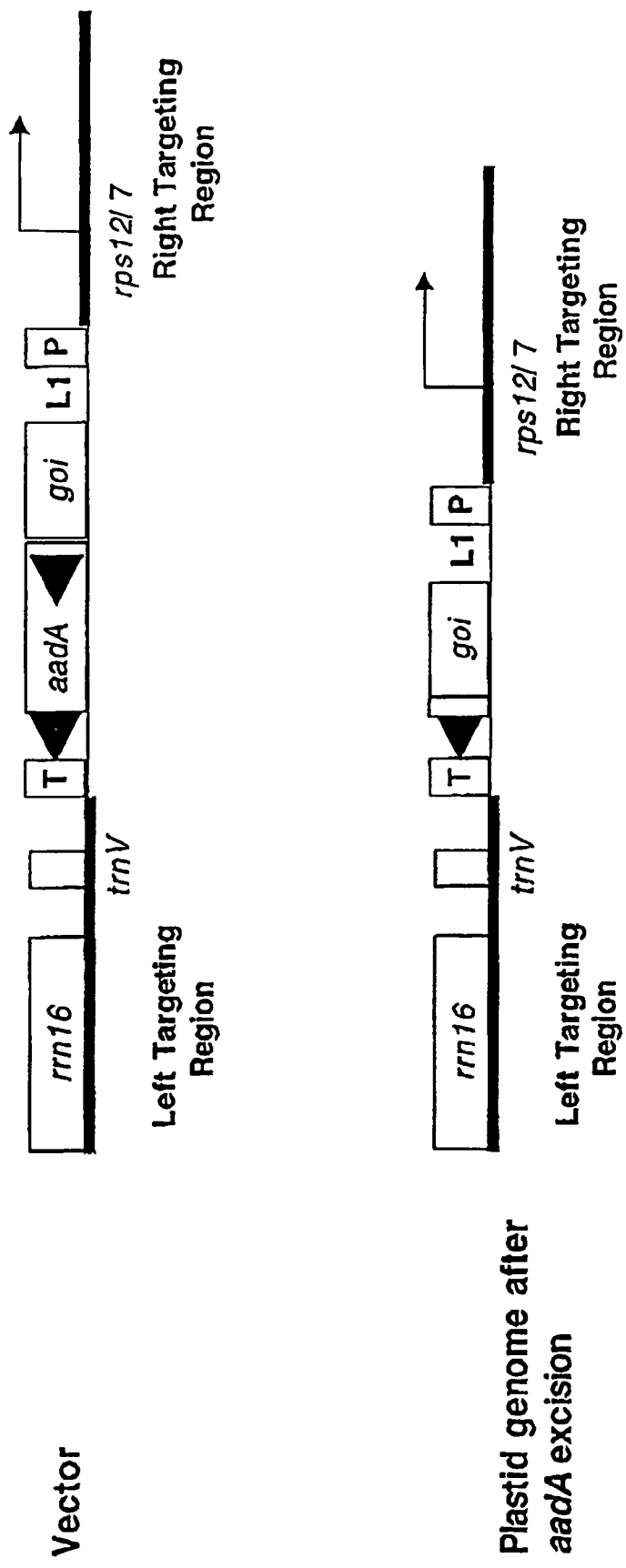
FIG. 18 shows a tobacco constitutive goi >aadA> dicistronic deletion vector, in which expression of aadA is dependent on translational coupling. Note that in this construct only one leader sequence is utilized. rrn16, trnV and rps12/7 are plastid genes (Shinozaki et al. 1986).

Maps of constitutive lox dicistronic deletion vectors are shown in FIG. 16 through FIG. 18. This dicistronic design enables simultaneous expression of both the first and the second open reading frames. The selectable marker designed for excision may be encoded in the first (FIG. 16) or second (FIG. 17, FIG. 18) open reading frames. Since a minimally 34 bp lox site is located between the two reading frames, both the marker gene (aadA) and the gene of interest have their own leader sequence to facilitate translation (FIG. 16, FIG. 17). Translational coupling may also be feasible if the lox site is incorporated in the marker gene coding region N terminus (FIG. 18). DNA sequence of promoter-lox constructs shown in FIG. 16 is set forth in Seq. ID No. 1. Promoters and promoter-leader combinations suitable to promote high-level protein expression in plastids are described in European Patent Applications WO 00/07421, WO 97/06250 and WO 98/55595. Sequences suitable for directly oriented lox sites are given in Seq. ID No. 11. Translational coupling between a gene of interest and the downstream aadA is shown in FIG. 18. There are multiple ways of achieving translational coupling between adjacent genes (Baneyx 1999). One approach is incorporation of a properly spaced ribosome binding-site in the upstream gene's coding region (Schoner et al. 1986; Omer et al.

1995). An example for a suitable sequence directly upstream of the translation initiation codon (ATG) would be G-GAG-GAA-TAA-CTT-ATG. A specific example for the use of the sequence is translational coupling between a bar (suitable source described in European Patent Application WO 00/07421) and a downstream aadA are given in Seq. ID No. 12. Note SalI site downstream of AUG incorporated to facilitate engineering the BglII-SalI region and the directly oriented lox sites in the aadA coding region and downstream of aadA. The sequence is given for a BglII-SpeI fragment. The BglII site is within the bar coding region; the SpeI site is downstream of the second lox site, as marked in FIG. 18. If a C-terminal extension to create a ribosome binding site is unacceptable, a suitable sequence may be obtained by silent mutagenesis of the coding region at the third codon position. Variants of plastid ribosome binding sites have been catalogued (Bonham-Smith and Bourque 1989)

Figure 19:
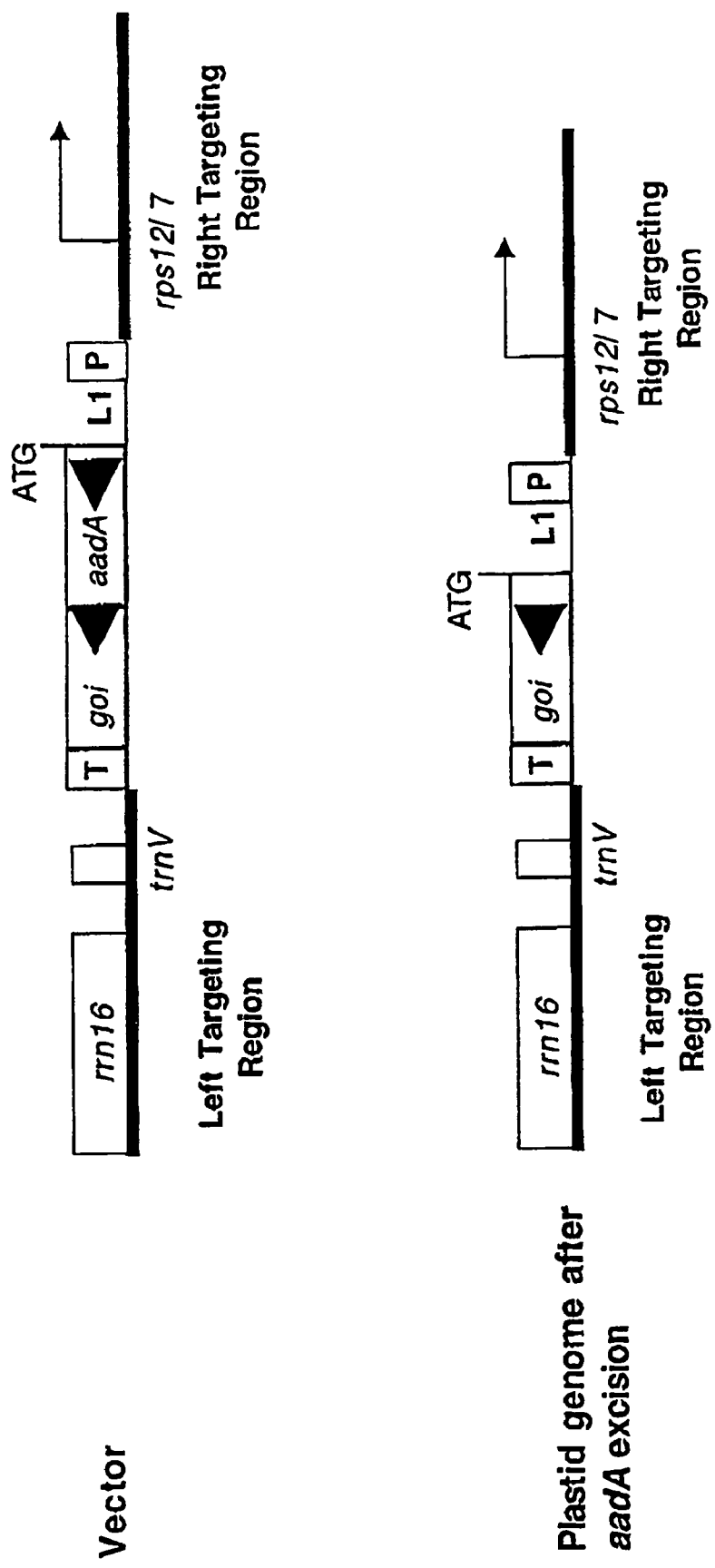
FIG. 19 shows a tobacco inducible lox deletion vector. Expression of goi is dependent on aadA excision. rrn16, trnV and rps12/7 are plastid genes (Shinozaki et al. 1986). Abbreviations: P, promoter; T, 3' untranslated region; L1 is 5' leader sequence.

A tobacco inducible lox deletion vector is shown in FIG. 19. The marker gene (aadA) is encoded in the first reading frame, followed by a silent goi lacking the translation initiation codon (ATG) and the 5' untranslated leader. Expression of the goi frame is triggered by aadA excision that results in translational fusion of the aadA N-terminal region with the goi. After aadA excision the goi mRNA is translated from the aadA translation control signals, the 5' UTR and AUG. DNA sequence of the SacI-NheI fragment is given in Seq. ID. No. 13. The Prrn promoter-atpB translational control region is described in European Patent Application WO 00/07421. The aadA construct has two directly-oriented lox sites: one in the coding region N-terminus and one downstream of aadA to facilitate CRE-mediated excision of the marker gene.

EXAMPLE 4

Deletion of Vital Plastid Genes to Obtain Cytoplasmic Male Sterility

U.S. Pat. No. 5,530,191 provides a cytoplasmic male sterility (CMS) system for plants, which is based on modification of the plastid genome. The CMS system comprises three transgenes: a "plastid male sterility" gene that causes plastid and cellular disablement of the anther tissue, and two nuclear genes that regulate the expression of the plastid gene. An important feature of the system is developmentally timed cellular death based on the expression, or the lack of the expression, of a plastid gene. As one specific approach to induce developmentally timed ablation of anther tissue we describe CRE-mediate excision of essential plastid genes via directly oriented lox sites.

The number of genes encoded by the plastid genome is about 120. Some of the genes are non-essential and may be inactivated by targeted gene disruption without a major phenotypic consequence. Good examples are the plastid ndh genes (Burrows et al. 1998; Shikanai et al. 1998) or the trnV gene the deletion of which has been described in Example 1. Excision of these genes is unlikely to cause cell ablation. The photosynthetic genes are essential for survival under field conditions. However, pigment deficient, non-photosynthetic plants can be maintained as long as they are grown on a sucrose-containing medium, or are grafted onto photosynthetically active wild-type (green) plants (Kanevski and Maliga 1994). Some of the house-keeping genes, such as the genes encoding the plastid multisubunit RNA polymerase are essential for photosynthetic growth, but not for survival (Allison et al. 1996). Thus, deletion of these genes is not suitable to trigger cell death. Only a relatively small number of plastid genes have proven to be essential for viability. The essential nature of the genes was recognized by the lack of homoplastomic cells in gene disruption experiments indicating that the loss of these genes results in cellular death. Cellular death due to lack of plastid function is understandable, as plastids are the site of the biosynthesis of amino acids, several lipids and are required for nitrate assimilation. Examples of plastid genes essential for cellular survival are the clpP protease subunit gene (Huang et al. 1994), ycf1 and ycf2, the two largest plastid-encoded open reading frames (Drescher et al. 2000).

Figure 20:
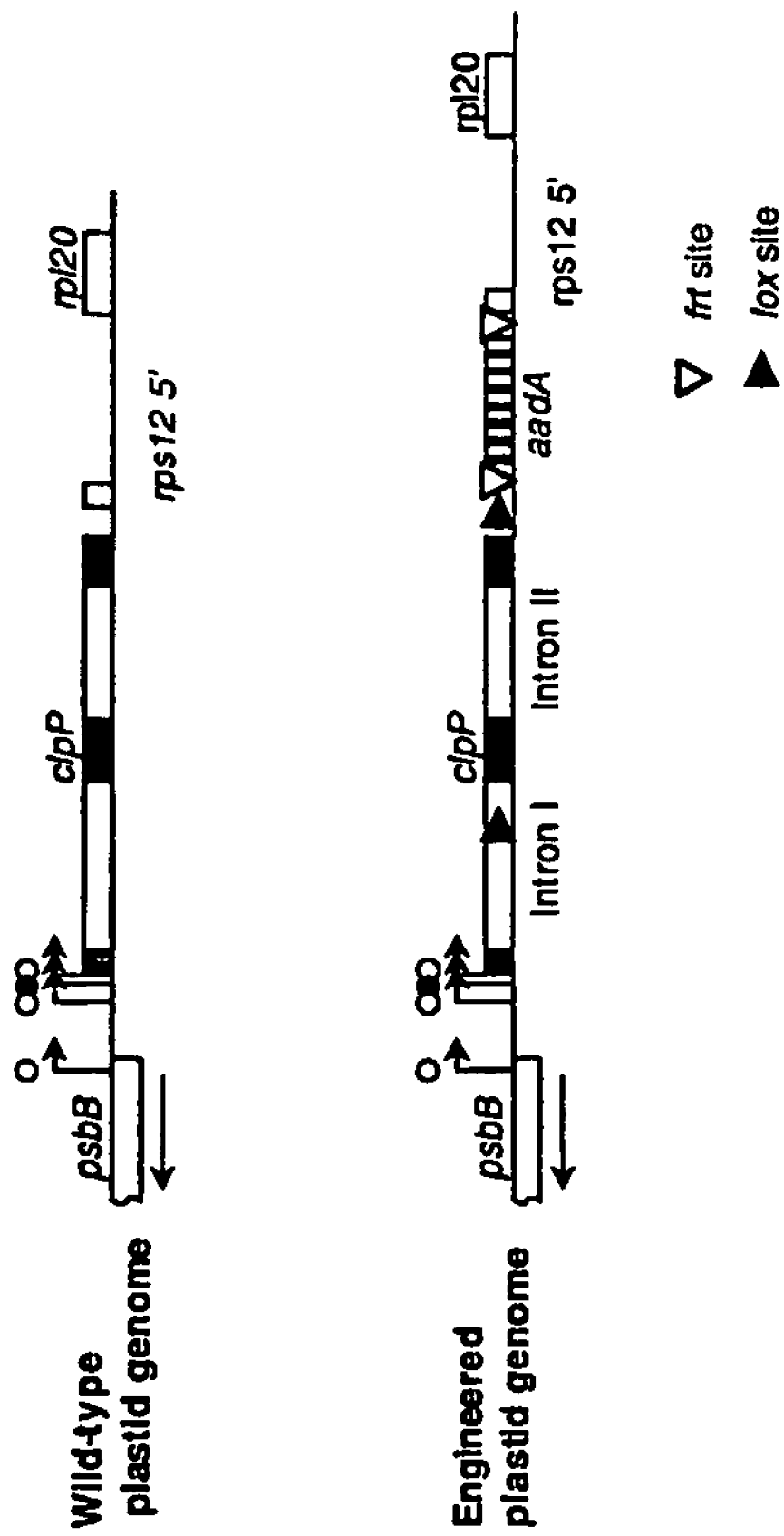
FIG. 20 shows a vector suitable for Cre-mediated deletion of clpP gene from the plastid genome. The region of engineered plastid genome shown is the sequence contained in the plastid transformation vector. The clpP Exons are dark boxes, the Introns are open boxes. Map position of plastid genes psbB, rps12 Exon I and rp120 is also shown.

To induce cellular death by CRE-mediated excision, directly oriented lox sites can be incorporated in the plastid genome flanking essential genes, as shown for clpP in FIG. 20. The clpP gene has two large introns (807 bp and 637 bp) and the region can be conveniently cloned as a SalI-SphI fragment. The selectable marker aadA is inserted into a KpnI restriction site created by PCR mutagenesis downstream of clpP Exon 3, oriented towards rps12 Exon I. One of the lox sites is engineered next to the aadA gene, the second lox site is inserted in Intron I. Cellular death is induced by activation of the nuclear Cre gene as described in U.S. Pat. No. 5,530,191. It is necessary to use a selective marker, such as aadA to introduce the lox sites into the plastid genome. The aadA gene can subsequently eliminated using a second, independent site specific recombinase such as FRT via the frt sites engineered into the transformation vector shown in FIG. 20.

Alternative targets for CRE-mediated deletion in a CMS system are the essential ribosomal protein genes such as rp123, the ribosomal RNA operon (for insertion sites see; Staub and Maliga 1992; Zoubenko et al. 1994) and the ycf1 and ycf2 genes (Drescher et al. 2000)

The following sequences are referred to throughout the specification and facilitate the practice of the present invention.

SEQ. No. 1: PrrnloxI. sequence gagctcGCTCCCCCGCCGTCGTTCAAT-GAGAATGGATAAGAGGCTCGTGGGATTGA CGT-GAGGGGGCAGGGATGGCTATATTTCTGG-GAGCataacttcgtataatgtatgc tatacgaagttatctaga SEQ. No. 2: TrbcLloxI. sequence gaattcataacttcgtatagcatacat-tatacgaagttatAGACATTAGCAGATAA ATTAGCAG-GAAATAAAGAAGGATAAGGAGAAA-GAACTCAAGTAATTATCCTTCGTT CTCTTAATTGAATTGCAATTAAACTCG-GCCCAATCTTTTACTAAAAGGATTGAGCC GAATA-CAACAAAGATTCTATTG-CATATATTTTGACTAAGTATATACTTACCTAGAT ATACAAGATTTGAAATACAAAATCTAGcaagcttggtacc SEQ. No. 3: cre coding region. sequence

```
gagctccATGgctagcTCC AATTTACTGA CCGTACACCA

AAATTTGCCT GCATTACCGG TCGATGCAAC GAGTGATGAG

GTTCGCAAGA ACCTGATGGA CATGTTCAGG GATCGCCAGG

CGTTTTCTGA GCATACCTGG AAAATGCTTC TGTCCGTTTG

CCGGTCGTGG GCGGCATGGT GCAAGTTGAA TAACCGGAAA

TGGTTTCCCG CAGAACCTGA AGATGTTCGC GATTATCTTC
```

-continued

TATATCTTCA GGCGCGCGGT CTGGCAGTAA AAACTATCCA

GCAACATTTG GGCCAGCTAA ACATGCTTCA TCGTCGGTCC

GGGCTGCCAC GACCAAGTGA CAGCAATGCT GTTTCACTGG

TTATGCGGCG GATCCGAAAA GAAAACGTTG ATGCCGGTGA

ACGTGCAAAA CAGGCTCTAG CGTTCGAACG CACTGATTTC

GACCAGGTTC GTTCACTCAT GGAAAATAGC GATCGCTGCC

AGGATATACG TAATCTGGCA TTTCTGGGGA TTGCTTATAA

CACCCTGTTA CGTATAGCCG AAATTCCCAG GATCAGGGTT

AAAGATATCT CACGTACTGA CGGTGGGAGA ATGTTAATCC

ATATTGGCAG AACGAAAACG CTGGTTAGCA CCGCAGGTGT

AGAGAAGGCA CTTAGCCTGG GGGTAACTAA ACTGGTCGAG

CGATGGATTT CCGTCTCTGG TGTAGCTGAT GATCCGAATA

ACTACCTGTT TTGCCGGGTC AGAAAAAATG GTGTTGCCGC

GCCATCTGCC ACCAGCCAGC TATCAACTCG CGCCCTGGAA

GGGATTTTTG AAGCAACTCA TCGATTGATT TACGGCGCTA

AGGATGACTC TGGTCAGAGA TACCTGGCCT GGTCTGGACA

CAGTGCCCGT GTCGGAGCCG CGCGAGATAT GGCCCGCGCT

GGAGTTTCAA TACCGGAGAT CATGCAAGCT GGTGGCTGGA

CCAATGTAAA TATTGTCATG AACTATATCC GTAACCTGGA

TAGTGAAACA GGGGCAATGG TGCGCCTGCT cGAgGATGGC

GATTAGtctaga

SEQ. No. 4: PrrnloxD. Sequence
gagctcGCTCCCCCGCCGTCGTTCAAT-
GAGAATGGATAAGAGGCTCGTGGGATTGA CGT-
GAGGGGGCAGGGATGGCTATATTTCTGG-
GAGCataacttcgtataatgtatgc tatacgaagttatgaattc SEQ. No. 5: TrbcLloxD. sequence
tctagataacttcgtataatgtatgc-
tatacgaagttatAGACATTAGCAGATAAA TTAGCAG-
GAAATAAAGAAGGATAAGGAGAAA-
GAACTCAAGTAATTATCCTTCGTTC
TCTTAATTGAATTGCAATTAAACTCGGC-
CCAATCTTTTACTAAAAGGATTGAGCCG AATACAA-
CAAAGATTCTATTGCATATATTTGAC-
TAAGTATATACTTACCTAGATA
TACAAGATTTGAAATACAAAATCTAGcaagcttggtacc SEQ. No. 6: Pea ssuTP5. sequence
ccggatccAA TTCAACCACA GAACTAACA AAGTCAGAAA

AATGGCTTCT ATGATATCCT CTTCCGCTGT GACAACAGTC

AGCCGTGCTT CTAGGGTGCA ATCCGCGGCA GTGGCTCCAT

TCGGCGGCCT GAAATCCATG ACTGGATTCC CAGTGAAGAA

GGTCAACACT GACATTACTT CCATTACAAG CAATGGTGGA

AGAGTAAAGT GCATGCAGGT GTGGCCTgcc atggctagc

SEQ. No. 7: Pea ssuTP22. sequence
ccggatcc AA TTCAACCACA GAACTAACA AAGTCAGAAA

AATGGCTTCT ATGATATCCT CTTCCGCTGT GACAACAGTC

AGCCGTGCTT CTAGGGTGCA ATCCGCGGCA GTGGCTCCAT

TCGGCGGCCT GAAATCCATG ACTGGATTCC CAGTGAAGAA

GGTCAACACT GACATTACTT CCATTACAAG CAATGGTGGA

AGAGTAAAGT GCATGCAGGT GTGGCCTCCA ATTGGAAAGA

AGAAGTTTGA GACTCTTTCC TATTTGCCAC CATTGACCat ggctagc

SEQ. No. 8: Pea ssuTP23. sequence
ccggatccAA TTCAACCACA GAACTAACA AAGTCAGAAA

AATGGCTTCT ATGATATCCT CTTCCGCTGT GACAACAGTC

AGCCGTGCTT CTAGGGTGCA ATCCGCGGCA GTGGCTCCAT

TCGGCGGCCT GAAATCCATG ACTGGATTCC CAGTGAAGAA

GGTCAACACT GACATTACTT CCATTACAAG CAATGGTGGA

AGAGTAAAGT GCATGCAGGT GTGGCCTCCA ATTGGAAAGA

AGAAGTTTGA GACTCTTTCC TATTTGCCAC CATTGACCAG

AGATCAGTTG gctagcgg

SEQ. No. 9: P2 promoter sequence
gaattCATTT TCACGTGTGG AAGATATGAA TTTTTTTGAG

AAACTAGATA AGATTAATGA ATATCGGTGT TTTGGTTTTT

TCTTGTGGCC GTCTTTGTTT ATATTGAGAT TTTTCAAATC

AGTGCGCAAG ACGTGACGTA AGTATCTGAG CTAGTTTTTA

TTTTTCTACT AATTTGGTCG TTTATTTCGG CGTGTAGGAC

ATGGCAACCG GGCCTGAATT TCGCGGGTAT TCTGTTTCTA

TTCCAACTTT TTCTTGATCC GCAGCCATTA ACGACTTTTG

AATAGATACG CTGACACGCC AAGCCTCGCT AGTCAAAAGT

GTACCAAACA ACGCTTTACA GCAAGAACGG AATGCGCGTG

ACGCTCGCGG TGACGCCATT TCGCCTTTTC AGAAATGGAT

AAATAGCCTT GCTTCCTATT ATATCTTCCC AAATTACCAA

TACATTACAC TAGCATCTGA ATTTCATAAC CAATCTCGAT

ACACCAAATC GATaggatcc taccatgg

SEQ. No. 10: 35S promoter sequence
AAGCTTGCCA ACATGGTGGA GCACGACACT CTCGTCTACT

CCAAGAATAT CAAAGATACA GTCTCAGAAG ACCAAAGGGC

TATTGAGACT TTTCAACAAA GGGTAATATC GGGAAACCTC

CTCGGATTCC ATTGCCCAGC TATCTGTCAC TTCATCAAAA

GGACAGTAGA AAAGGAAGGT GGCACCTACA AATGCCATCA

TTGCGATAAA GGAAAGGCTA TCGTTCAAGA TGCCTCTGCC

GACAGTGGTC CCAAAGATGG ACCCCCACCC ACGAGGAGCA

TCGTGGAAAA AGAAGACGTT CCAACCACGT CTTCAAAGCA

AGTGGATTGA TGTGATAACA TGGTGGAGCA CGACACTCTC

```
GTCTACTCCA AGAATATCAA AGATACAGTC TCAGAAGACC

AAAGGGCTAT TGAGACTTTT CAACAAAGGG TAATATCGGG

AAACCTCCTC GGATTCCATT GCCCAGCTAT CTGTCACTTC

ATCAAAAGGA CAGTAGAAAA GGAAGGTGGC ACCTACAAAT

GCCATCATTG CGATAAAGGA AAGGCTATCG TTCAAGATGC

CTCTGCCGAC AGTGGTCCCA AAGATGGACC CCCACCCACG

AGGAGCATCG TGGAAAAAGA AGACGTTCCA ACCACGTCTT

CAAAGCAAGT GGATTGATGT GATATCTCCA CTGACGTAAG

GGATGACGCA CAATCCCACT ATCCTTCGCA AGACCCTTCC

TCTATATAAG GAAGTTCATT TCATTTGGAG AGGACACGCT

GAAATCACCA GTCTCTCTCT ACAAATCTAT CTCTCTCGAT

TCGCGAGCTC GGTACCCGGG gatcgatcc
```

SEQ. No. 11: KpnI-lox-BglII-lox-HindIII fragment ggtaccATAACTTCGTATAATGTATGC-
TATACGAAGTTATagatctATAACTTCGT ATAATGTAT-
GCTATACGAAGTTATaagctt

```
Seq. ID No. 12. Translational coupling of bar and
aadA according to scheme in FIG. 18. BglII-SpeI
fragment.

GAGATCTGgg aggaataact tATGggggtc gacATAACTT

CGTATAATGT ATGCTATACG AAGTTATtaG AAGCGGTGAT

CGCCGAAGTA TCGACTCAAC TATCAGAGGT AGTTGGCGTC

ATCGAGCGCC ATCTCGAACC GACGTTGCTG GCCGTACATT

TGTACGGCTC CGCAGTGGAT GGCGGCCTGA AGCCACACAG

TGATATTGAT TTGCTGGTTA CGGTGACCGT AAGGCTTGAT

GAAACAACGC GGCGAGCTTT GATCAACGAC CTTTTGGAAA

CTTCGGCTTC CCCTGGAGAG AGCGAGATTC TCCGCGCTGT

AGAAGTCACC ATTGTTGTGC ACGACGACAT CATTCCGTGG

CGTTATCCAG CTAAGCGCGA ACTGCAATTT GGAGAATGGC

AGCGCAATGA CATTCTTGCA GGTATCTTCG AGCCAGCCAC

GATCGACATT GATCTGGCTA TCTTGCTGAC AAAAGCAAGA

GAACATAGCG TTGCCTTGGT AGGTCCAGCG GCGGAGGAAC

TCTTTGATCC GGTTCCTGAA CAGGATCTAT TTGAGGCGCT

AAATGAAACC TTAACGCTAT GGAACTCGCC GCCCGACTGG

GCTGGCGATG AGCGAAATGT AGTGCTTACG TTGTCCCGCA

TTTGGTACAG CGCAGTAACC GGCAAAATCG CGCCGAAGGA

TGTCGCTGCC GACTGGGCAA TGGAGCGCCT GCCGGCCCAG

TATCAGCCCG TCATACTTGA AGCTAGACAG GCTTATCTTG

GACAAGAAGA AGATCGCTTG GCCTCGCGCG CAGATCAGTT

GGAAGAATTT GTCCACTACG TGAAAGGCGA GATCACCAAG

GTAGTCGGCA AATAAATAAC TTCGTATAAT GTATGCTATA

CGAAGTTATa ctagt
```

Seq. ID No. 13. CRE-induced expression of recombinant protein according to design in FIG. 19. SacI-NheI fragment.

```
gagctcGCTC CCCCGCCGTC GTTCAATGAG AATGGATAAG

AGGCTCGTGG GATTGACGTG AGGGGGCAGG GATGGCTATA

TTTCTGGGAG AATTAACCGA TCGACGTGCa AGCGGACATT

TATTTTaAAT TCGATAATTT TTGCAAAAAC ATTTCGACAT

ATTTATTTAT TTTATTATTA TGgggATAAC TTCGTATAAT

GTATGCTATA CGAAGTTATt aGAAGCGGTG ATCGCCGAAG

TATCGACTCA ACTATCAGAG GTAGTTGGCG TCATCGAGCG

CCATCTCGAA CCGACGTTGC TGGCCGTACA TTTGTACGGC

TCCGCAGTGG ATGGCGGCCT GAAGCCACAC AGTGATATTG

ATTTGCTGGT TACGGTGACC GTAAGGCTTG ATGAAACAAC

GCGGCGAGCT TTGATCAACG ACCTTTTGGA AACTTCGGCT

TCCCCTGGAG AGAGCGAGAT TCTCCGCGCT GTAGAAGTCA

CCATTGTTGT GCACGACGAC ATCATTCCGT GGCGTTATCC

AGCTAAGCGC GAACTGCAAT TTGGAGAATG GCAGCGCAAT

GACATTCTTG CAGGTATCTT CGAGCCAGCC ACGATCGACA

TTGATCTGGC TATCTTGCTG ACAAAAGCAA GAGAACATAG

CGTTGCCTTG GTAGGTCCAG CGGCGGAGGA ACTCTTTGAT

CCGGTTCCTG AACAGGATCT ATTTGAGGCG CTAAATGAAA

CCTTAACGCT ATGGAACTCG CCGCCCGACT GGGCTGGCGA

TGAGCGAAAT GTAGTGCTTA CGTTGTCCCG CATTTGGTAC

AGCGCAGTAA CCGGCAAAAT CGCGCCGAAG GATGTCGCTG

CCGACTGGGC AATGGAGCGC CTGCCGGCCC AGTATCAGCC

CGTCATACTT GAAGCTAGAC AGGCTTATCT TGGACAAGAA

GAAGATCGCT TGGCCTCGCG CGCAGATCAG TTGGAAGAAT

TTGTCCACTA CGTGAAAGGC GAGATCACCA AGGTAGTCGG

CAAATAAATA ACTTCGTATA ATGTATGCTA TACGAAGTTA

Ttagctagc
```

REFERENCES

Adams D E, Bliska J B, Cozzarelli N R (1992) Cre-lox recombination in *Escherichia coli* cells. Mechanistic differences from the in vitro reaction. J Mol Biol 50 226: 661–673

Albert H, Dale E C, Lee E, Ow D W (1995) Site-specific integration of DNA into wild-type and mutant lox sites placed in the plant genome. Plant J 7:649–659

Allison L A, Simon L D, Maliga P (1996) Deletion of rpoB reveals a second distinct transcription system in plastids of higher plants. EMBO J. 15:2802–2809

Aoyama T, Chau N H (1997) A glucocorticoid-mediated transcriptional induction system in transgenic plants. Plant J 11:605–612

Baneyx F (1999) Recombinant protein expression in *Escherichia coli*. Curr Opin Biotechnol 10:411–421

Beck C F, Ingraham J L, Neuhard J, Thomassen E (1972) Metabolism of pyrimidines and pyrimidine nucleosides by *Salmonella typhimurium*. J Bacteriol 110:219–228

Bonham-Smith P C, Bourque D P (1989) Translation of chloroplast-encoded mRNA: potential initiation and termination signals. Nucleic Acids Res 17:2057–2080

Burrows P A, Sazanov L A, Svab Z, Maliga P, Nixon P J (1998) Identification of a functional respiratory complex in chloroplasts through analysis of tobacco mutants containing disrupted plastid ndh genes. EMBO J. 17:868–876

Carrer H, Hockenberry T N, Svab Z, Maliga P (1993) Kanamycin resistance as a selectable marker for plastid transformation in tobacco. Mol Gen Genet 241:49–56

Carrer H, Maliga P (1995) Targeted insertion of foreign genes into the tobacco plastid genome without physical linkage to the selectable marker gene. Biotechnology 13:791–794

Carrer H, Staub J M, Maliga P (1990) Gentamycin resistance in *Nicotiana* conferred by AAC(3)-I, a narrow substrate specificity acetyl transferase. Plant Mol Biol 17:301–303

Craig N L (1988) The mechanism of conservative site-specific recombination. Annual Review Of Genetics 22:77–105

Dale E C, Ow D W (1991) Gene transfer with subsequent removal of the selection gene from the host genome. Proc Natl Acad Sci USA 88:10558–10562

Depicker A G, Jacobs A M, Montagu M C (1988) A negative selection scheme for tobacco protoplast-derived cells expressing the T-DNA gene 2. Plant Cell Rep 7:63–66

Drescher A, Ruf S, Calsa T, Carrer H, Bock R (2000) The two largest chloroplast genome-encoded open reading frames of higher plants are essential genes. The Plant Journal 22:97–104

Držge M, PŸhler A, Selbitschka W (1998) Horizontal gene transfer as a biosafety issue: a natural phenomenon of public concern. J Biotechnol 64:75–90

Gatz C (1997) Chemical control of gene expression. Ann Rev Plant Physiol Plant Mol Biol 48:89–108

Gatz C, Frohberg C, Wendenburg R (1992) Stringent repression and homogeneous de-repression by tetracycline of a modified CaMV 35S promoter in intact transgenic tobacco plants. Plant J 2:397–404

Hajdukiewicz P, Svab Z, Maliga P (1994) The small, versatile pPZP family of *Agrobacterium* binary vectors for plant transformation. Plant Mol Biol 25:989–994

Hoess R H, Ziese M, Sternberg N (1982) P1 site-specific recombination: nucleotide sequence of the recombining sites. Proc Natl Acad Sci USA 79:3398–3402

Huang C, Wang S, Chen L, Lemioux C, Otis C, Turmel M, Liu X Q (1994) The *Chlamydomonas* chloroplast clpP gene contains translated large insertion sequences and is essential for cell growth. Molecular and Genetal Genetics 244:151–159

Kanevski I, Maliga P (1994) Relocation of the plastid rbcL gene to the nucleus yields functional ribulose-1,5-bisphosphate carboxylase in tobacco chloroplasts. Proc Natl Acad Sci USA 91:1969–1973

Karlin-Neumann G A, Brusslan J A, Tobin E M (1991) Phytochrome control of the tms2 gene in transgenic *Arabidopsis*: a strategy for selecting mutants in the signal transduction pathway. Plant Cell 3:573–582

Khan M S, Maliga P (1999) Fluorescent antibiotic resistance marker to track plastid transformation in higher plants. Nat Biotechnol 17:910–915

Kolb A F, Siddell S G (1996) Genomic targeting with an MBP-Cre fusion protein [published erratum appears in Gene 1997 Apr. 11; 189(1):149]. gene 183:53–60

Le Y, Gagneten S, Tombaccini D, Bethke B, Sauer B (1999) Nuclear targeting determinants of the phage P1 Cre DNA recombinase. Nucleic Acids Res 27:4703–4709

Lichtenstein C, Barrena E (1993) Prospects for reverse genetics in plants using recombination [news]. Plant Mol Biol 21:v–xii Love J, Scott A C, Thompson W F (2000) Stringent control of transgene expression in *Arabidopsis thaliana* using the Top10 promoter system. Plant J 21:579–588

Lubben T H, Gatenby A A, Ahlquist P, Keegstra K (1989) Chloroplast import characteristics of chimeric proteins. Plant Mol Biol 12:13–18

Lyznik L A, Hirayama L, Rao K V, Abad A, Hodges T K (1995) Heat-inducible expression of FLP gene in maize cells. Plant J 8:177–186

Lyznik L A, Mitchell J C, Hirayama L, Hodges T K (1993) Activity of yeast FLP recombinase in maize and rice protoplasts. Nucleic Acids Res 21:969–975

Lyznik L A, Rao K V, Hodges T K (1996) FLP-mediated recombination of FRT sites in the maize genome. Nucleic Acids Res 24:3784–3789

Maliga P (1993) Towards plastid transformation in higher plants. Trends Biotech 11:101–107

Martinez A, Sparks C, Hart C A, Thompson J, Jepson I (1999) Ecdysone agonist inducible transcription in transgenic tobacco plants. Plant J 19:97–106

Mett V L, Lochhead L P, Reynolds P H S (1993) Copper-controllable gene expression for whole plants. Proc Natl Acad Sci USA 90:4567–4571

Morris A C, Schaub T L, James A A (1991) FLP-mediated recombination in the vector mosquito, *Aedes aegypti*. Nucleic Acids Res 19:5895–5900

Nussaume L, Vincentz M, Caboche M (1991) Constitutive nitrate reductase: a dominant conditional marker for plant genetics. Plant J 1:267–274

O'Gorman S, Fox D T, Wahl G M (1991) Recombinase-mediated gene activation and site-specific integration in mammalian cells. Science 251:1351–1355

Omer C A, Diehl R E, Kral A M (1995) Bacterial expression and purification of human protein prenyltransferases using epitope-tagged, translationally coupled systems. Meth Enzymol 250:3–12

Perera R J, Linard C G, Signer E R (1993) Cytosine deaminase as a negative selective marker for *Arabidopsis*. Plant Mol Biol 23:793–799

Russell S H, Hoopes J L, Odell J T (1992) Directed excision of a transgene from the plant genome. Mol Gen Genet 234:49–59

Schoner B E, Belagaje R M, Schoner R G (1986) Translatrion of a synthetic two-cidstron mRNA in *Escherichia coli*. Proc Natl Acad Sci USA 83:8506–8510

Serino G, Maliga P (1997) A negative selection scheme based on the expression of cytosine deaminase in plastids. Plant J 12:697–701

Shikanai T, Endo T, Hashimoto T, Yamada Y, Asada K, Yokota A (1998) Directed disruption of the tobacco ndhB gene impairs cyclic electron flow around photosystem I. Proc Natl Acad Sci USA 95:9705–9709

Shinozaki K, Ohme M, Tanaka M, Wakasugi T, Hayashida N, Matsabayashi T, Zaita N, Chungwongse J, Obokata J, Yamaguchi-Shinozaki K, Deno H, Kamogashira T, Yamada K, Kasuda J, Takaiwa F, Kato A, Todoh N, Shimada H, Sugiura M (1986) The complete sequence of the tobacco chloroplast genome: its gene organization and expression. EMBO J. 5:2043–2049

Small I, Wintz H, Akashi K, Mireau H (1998) Two birds with one stone: genes that encode products targeted to two or more compartments. Plant Mol Biol 38:265–277

Soll J, Tien R (1998) Protein translocation into and across the chloroplastic envelope membranes. Plant Mol Biol 38:191–207

Sriraman P (2000) Identification and characterization of components of the plastid transcription machinery. Identification and characterization of components of the plastid transcription machinery. Rutgers University, Piscataway, N.J.

Srivastava V, Anderson O D, Ow D W (1999) Single-copy transgenic wheat generated trough the resolution of complex integration patterns. Proceedings of the National Academy of Sciences 96:11117–11121

Staub J M, Maliga P (1992) Long regions of homologous DNA are incorporated into the tobacco plastid genome by transformation. Plant Cell 4:39–45

Staub J M, Maliga P (1995) Expression of a chimeric uida gene indicates that polycistronic mRNAs are efficiently translated in tobacco plastids. Plant J 7:845–848

Stougaard J (1993) Substrate-dependent negative selection in plants using a bacterial cytosine deaminase gene. Plant J 3:755–761

Stricklett P K, Nelson R D, Kohan D E (1998) Site-specific recombination using an epitope tagged bacteriophage P1 Cre recombinase. gene 215:415–423

Sundaresan V, Springer P, Volpe T, Haward S, Jones J D, Dean C, Ma H, Martienssen R (1995) Patterns of gene action in plant development revealed by enhancer trap and gene trap transposable elements. Genes Dev 9:1797–1810

Svab Z, Harper E C, Jones J D, Maliga P (1990) Aminoglycoside-3I'-adenyltransferase confers resistance to spectinomycin and streptomycin in Nicotiana tabacum. Plant Mol Biol 14:197–205

Svab Z, Maliga P (1993) High-frequency plastid transformation in tobacco by selection for a chimeric aadA gene. Proc Natl Acad Sci USA 90:913–917

Sylvanen M (1999) In search of horizontal gene transfer. Nat Biotechnol 17:833

Tepfer D (1989) R1 T-DNA from *Agrobacterium rhizogenes*: a source of genes having applications in rhizosphere biology and plant development, ecology and evolution. In: Kosuge T, Nester E W (eds) *Plant-Microbe Interactions. Molecular and Genetic Perspectives*, Vol. 3, McGraw-Hill, New York, pp 294–342

Timko M P, Kaush A P, Hand J M, Cashmore A R (1985) Structure and expression of nuclear genes encoding polypeptides of the photosynthetic apparatus. In: Steinback K E, Bonitz S, Arntzen C J, Bogorad L (eds) Molecular biology of the photosynthetic apparatus., Cold Spring Harbor Laboratory, Cold Spring Harbor, pp 381–396.

Timmermans M C P, Maliga P, Vieira J, Messing J (1990) The pFF plasmids: cassettes utilizing CaMV sequences for expression of foreign genes in plants. J Biotechnol 14:333–344.

van Haaren M J, Ow D W (1993) Prospects of applying a combination of DNA transposition and site-specific recombination in plants: a strategy for gene identification and cloning. Plant Mol Biol 23:525–533

Velten J, Velten L, Hain R, Schell J (1984) Isolation of a dual plant promoter fragment from the Ti plasmid of *Agrobacterium tumefaciens*. EMBO J. 3:2723–2730.

Wasmann C C, Reiss B, Bartlett S G, Bohnert H J (1986) The import of the ransit peptide and the transportrf protein for protein import into chloroplasts. Mol Gen Genet 205:446–453

Wimmer B, Lottspeich F, van der Klei I, Veenhuis M, Gietl C (1997) The glyoxysomal and plastid molecular chaperones (70-kDa heat shock protein) of watermelon cotyledons are encoded by a single gene. Proc Natl Acad Sci USA 94:13624–13629

Xiang C, Guerra D J (1993) The anti-nptII gene. A potential negative selective marker for plants. Plant Physiol 102: 287–293

Zoubenko O V, Allison L A, Svab Z, Maliga P (1994) Efficient targeting of foreign genes into the tobacco plastid genome. Nucleic Acids Res 22:3819–3824

While certain of the preferred embodiments of the present invention have been described and specifically exemplified above, it is not intended that the invention be limited to such embodiments. Various modifications may be made thereto without departing from the scope and spirit of the present invention, as set forth in the following claims.

What is claimed is:

1. A site specific recombination method for removal of predetermined nucleic acid sequences from the plastid genome, said method comprising:

a) providing a first nucleic acid construct, said construct comprising a promoter being operably linked to a nucleic acid encoding plastid targeting transit sequence which is operably linked to a nucleic acid encoding a site specific recombinase having excision activity, said construct further comprising a first selectable marker encoding nucleic acid having plant specific 5' and 3' regulatory nucleic acid sequences;

b) providing a second DNA construct, said second construct comprising an second selectable marker encoding nucleic acid sequence which is flanked by excision sites, said second construct optionally containing a gene of interest, said second construct further comprising flanking plastid targeting nucleic acid sequences which facilitate homologous recombination into said plastid genome;

c) introducing said second DNA construct into a plant cell;

d) culturing said plant cell of step c) in the presence of a selection agent, thereby selecting for those plant cells expressing the proteins encoded by said second DNA construct; e) introducing said first DNA construct into plant cells from step d) in the presence of a selection agent and selecting those plant cells expressing proteins encoded by said first construct, which when present said site specific recombinase acts on said excision sites, thereby removing said sequence flanked by said excision sites from said plastid genome.

2. A method as claimed in claim 1, wherein a plant is regenerated from plant cells of step c), cells are then contacted with said first construct and steps d) and e) are performed.

3. A method as claimed in claim 1, wherein said first construct is that depicted in FIG. 3.

4. A method as claimed in claim 1, wherein said second construct is that depicted in FIG. 2.

5. A method as claimed in claim 1, wherein said site specific recombinase is selected from the group consisting of CRE, flippase, resolvase, FLP, SSV1-encoded integrase, and transposase.

6. A method as claimed in claim 1, wherein said excision sites are LOX sequences when CRE recombinase is used and frt sequences when FLP recombinase is used.

7. A method as claimed in claim 1, wherein said selection agent is selected from the group consisting of kanamycin, gentamycin, spectinomycin, streptomycin and hygromycin, phosphinotricin, basta, glyphosate and bromoxynil.

8. A method as claimed in claim 1, wherein said excision of said predetermined sequence creates an expressible translational fusion protein.

9. A method as claimed in claim 1, wherein said predetermined nucleic acid sequence is the selectable marker encoding nucleic acid present in said second construct.

10. A plant regenerated from the plant cells of step e) of claim 1.

11. A site specific recombination system comprising the constructs of the method of claim 1.

12. A site specific recombination method for removal of predetermined nucleic acid sequences from a plastid genome, said method comprising:
   a) providing a first nucleic acid construct, said construct comprising a regulated promoter being operably linked to a nucleic acid encoding a plastid targeting transit sequence which is operably linked to a nucleic acid encoding a site specific recombinase having excision activity, said construct optionally further comprising a first selectable marker encoding nucleic acid having plant specific 5' and 3' regulatory nucleic acid sequences;
   b) providing a second DNA construct, said second construct comprising a second selectable marker encoding nucleic acid, said second construct further comprising flanking plastid targeting nucleic acid sequences which flank a pair of excision sites, the second selectable marker encoding nucleic acid, and a predetermined nucleic acid sequence from a plastid genome, wherein the excision sites flank the second selectable marker encoding nucleic acid and the predetermined nucleic acid sequence, wherein said plant targeting nucleic acid sequences facilitate homologous recombination into said plastid genome comprising said predetermined sequence targeted for deletion;
   c) introducing said second DNA construct into a plant cell and allowing said homologous recombination to occur;
   d) culturing a plant cell of step c) in the presence of a selection agent, thereby selecting for those plant cells expressing the proteins encoded by said second DNA construct;
   e) regenerating a plant from cells obtained in step d);
   f) introducing said first DNA construct into plant cells from the plant of step e) in the presence of a selection agent and selecting those plant cells expressing proteins encoded by said first construct, which when present said site specific recombinase acts on said excision sites, thereby removing said predetermined nucleic acid sequence and said second selectable marker nucleic acid sequence from the plastid genome.

13. A method as claimed in claim 12, wherein said regulatable promoter is selected from the group of promoters consisting of inducible promoters, tissue specific promoters, developmentally regulated promoters and chemically inducible promoters.

14. A method as claimed in claim 12, wherein said predetermined target sequence is selected from the group consisting of male sterility genes, clpP ribosomal protein-encoding genes, and ribosomal RNA operon sequences.

15. A method as claimed in claim 12, wherein said protein having excision activity is selected from the group consisting of CRE, flippase, resolvase, FLP, SSV1-encoded integrase, and transposase.

16. A method as claimed in claim 12, wherein said excision sites are LOX sequences when CRE recombinase is used, and frt sequences when FLP recombinase is used.

17. A method as claimed in claim 12, wherein said selection agent is selected from the group consisting of kanamycin, gentamycin, spectinomycin, streptomycin and hygromycin, phosphinotricin, basta, glyphosate and bromoxynil.

18. A plant regenerated from the plant cells of step f) of claim 12.

19. A site specific recombination system for removal of predetermined nucleic acid sequences comprising the constructs of claim 12.

20. Progeny plants obtained from the plant of claim 10.

21. Progeny plants obtained from the plant of claim 18.

* * * * *